United States Patent [19]

Scott et al.

[11] 4,026,907

[45] May 31, 1977

[54] ANTIOXIDANT CHROMAN COMPOUNDS

[75] Inventors: John William Scott, Upper Montclair; David Richard Parrish, Glen Ridge; Gabriel Saucy, Essex Fells, all of N.J.

[73] Assignee: Hoffmann-La Roche Inc., Nutley, N.J.

[22] Filed: Dec. 4, 1975

[21] Appl. No.: 637,548

Related U.S. Application Data

[60] Division of Ser. No. 417,465, Nov. 19, 1973, Pat. No. 3,947,473, which is a continuation-in-part of Ser. No. 317,566, Dec. 22, 1972, abandoned.

[52] U.S. Cl. .......................................... 260/345.5
[51] Int. Cl.² ..................................... C07D 311/72
[58] Field of Search ................................ 260/345.5

[56] References Cited

OTHER PUBLICATIONS

Mayer et al., Helv. Chim. Acta, 46, 650 (1963).
Weichet et al., Coll. Czech. Chem. Comm., 24, 1689 (1959).
McOmie, Adv. in Org. Chem., vol. 3, pp. 216–233 (1963).

*Primary Examiner*—James O. Thomas, Jr.
*Assistant Examiner*—Nicky Chan
*Attorney, Agent, or Firm*—Samuel L. Welt; Bernard S. Leon; Richard A. Gaither

[57] ABSTRACT

The (6-hydroxy-chroman-2-yl) acetic or carboxylic acid derivatives useful as antioxidants and a method for preparing these derivatives from hydroquinones and intermediates in this synthesis as well as the use of these derivatives as intermediates in the preparation of optically active alpha-tocopherol.

2 Claims, No Drawings

ANTIOXIDANT CHROMAN COMPOUNDS

CROSS REFERENCE TO RELATED APPLICATIONS

This application is a division of application Ser. No. 417,465, filed Nov. 19, 1973, now U.S. Pat. No. 3,947,473, which in turn is a continuation-in-part of application Ser. No. 317,566, filed Dec. 22, 1972, now abandoned.

SUMMARY OF THE INVENTION

In accordance with this invention, it has been discovered that compounds of the formula:

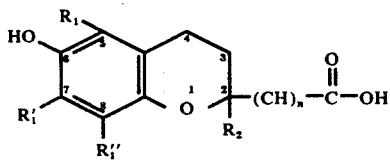

wherein $R_1$, $R_1'$ and $R_1''$ are independently hydrogen or lower alkyl; $R_2$ is hydrogen, lower alkyl or phenyl; and n is an integer from 0 to 1; including racemates and optical antipodes thereof are valuable antioxidants for stabilizing organic materials normally susceptible to oxidation.

Furthermore, in accordance with this invention there is provided a process for preparing the compound of formula I either in its racemic 2RS form or in either of its optically active 2R or 2S forms.

Furthermore, the compounds of formula I are intermediates for preparing alpha-tocopherol. The compound of formula I, depending upon whether this compound is in its 2R, 2S or 2RS form can be utilized as an intermediate in preparing natural optically active alpha-tocopherol, i.e., alpha-tocopherol having the 2R, 4'R, and 8'R configuration as well as alpha-tocopherols having the following configurations:

2R, 4'RS, 8'RS;
2S, 4'R, 8'R';
2S, 4'RS, 8'RS;
2RS, 4'RS, 8'RS; and
2RS, 4'R, 8'R.

Therefore, the use of the process of this invention provides a simple and economic method for stereospecifically synthesizing alpha-tocopherol from trimethylhydroquinone. In Helv. Chim. Acta, 46, 650 (1963), Mayer et al., a chemical synthesis of optically active alpha-tocopherol from trimethylhydroquinone was reported. However, the yield of optically active alpha-tocopherol produced by this process was very low since it involved the step of ozonolysis. In this step, there was a great loss of yield due to the destruction of the chroman nucleus when it underwent ozonolysis. On the other hand, the process of this invention utilizing the compound of formula I where $R_1$, $R_2$, $R_1'$ and $R_1''$ are methyl as an intermediate, avoids any ozonolysis step and produces alpha-tocopherol with a desired stereo-configuration in high yields.

DETAILED DESCRIPTION OF THE INVENTION

The numbering of the chroman ring in the compound of formula I is given for the purpose of convenience.

As used throughout this application, the term "lower alkyl" includes both straight chain and branched chain alkyl groups having from 1 to 7 carbon atoms, such as methyl, ethyl and propyl, preferably methyl. As used herein, the term "lower alkoxy" comprehends groups having from 1 to 7 carbon atoms, such as methoxy and ethoxy. As also used herein, the term "lower alkanoic acids" comprehends an alkanoic acid of 2 to 7 carbon atoms such as acetic acid and propionic acid. As further used herein, the term "halogen" or "halo", unless otherwise stated, comprehends fluorine, chlorine, bromine and iodine. The term "lower alkylenedioxy" designates lower alkylenedioxy groups containing from 2 to 6 carbon atoms such as ethylenedioxy.

As also used herein, the term "aryl" signifies mononuclear aromatic hydrocarbon groups such as phenyl, tolyl, etc., which can be unsubstituted or substituted in one or more positions with a lower alkylenedioxy, a halogen, a nitro, a lower alkyl or a lower alkoxy substituent, and polynuclear aryl groups such as naphthyl, anthryl, phenanthryl, azulyl, etc., which can be unsubstituted or substituted with one or more of the aforementioned groups. The preferred aryl groups are the substituted and unsubstituted mononuclear aryl groups, particularly phenyl. The term "aryl lower alkyl" comprehends groups wherein aryl and lower alkyl are as defined above, particularly benzyl. The term "aryl lower alkanoic acid" comprehends acids wherein "aryl" and "lower alkanoic acid" are as defined above, particularly benzoic acid. As used herein, the term "ester protecting group removable by hydrolysis" designates any ester which can be hydrolyzed to yield the hydroxy group. Exemplary ester groups useful for this purpose are those in which the acyl moiety is derived from a lower alkanoic, an aryl lower alkanoic, phosphoric, carbonic or a lower alkane dicarboxylic acid. Among the acids which can be utilized to form such ester groups are the acid anhydrides and the acid halides, preferably chlorides or bromides, with the lower alkanoic acid anhydrides, e.g., acetic anhydride and caproic anhydride, the aryl lower alkanoic acid anhydrides, e.g., benzoic acid anhydrides, lower alkane dicarboxylic acid anhydrides, e.g., succinic anhydride, and chloroformates, e.g., trichloroethylchloroformate, being preferred. The term "ether protecting group removable by hydrogenolysis or hydrolysis" designates any ether which, upon hydrogenolysis or hydrolysis yields the hydroxy group. A suitable ether protecting group is the arylmethyl ether such as benzyl, benzylhydryl or tritryl ethers or alpha-lower alkoxy lower alkyl ether, for example, methoxymethyl, tetrahydropyranyl or allylic ethers.

In the structural formule given throughout this application, the substituents attached to the molecule above the plane of the molecule are designate by ▲, and the substituents attached to the molecule below the plane of the molecule are designated by ≡. In the structural formulae given throughout the application where no stereoorientation is indicated, the substituents in the compound designated thereby can be either in their R or S orientation or the compound can be a mixture of R and S isomers.

The compound of formula I where n is 1, has the formula:

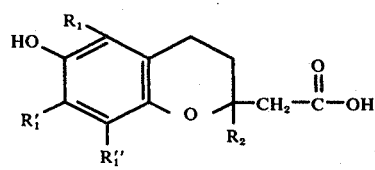

where $R_1$, $R_1'$, $R_1''$ and $R_2$ are as above; and the compound of formula I where n is 0 has the formula:

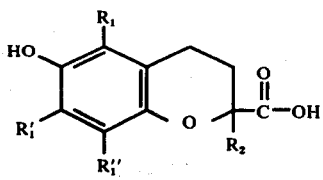
                                                                I-B wherein $R_1$, $R_1'$, $R_1''$ and $R_2$ are as above.

The compounds of formulae I-A and I-B can be prepared from an intermediate of the formula:

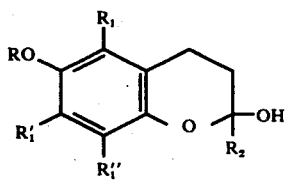
                                                                II wherein R is hydrogen or forms an ether protecting group removable by hydrogenolysis or hydrolysis or an ester protecting group removable by hydrolysis; and $R_1$, $R_1'$, $R_1''$ and $R^2$ are as above.

In the first step of preparing the compound of formula II, a hydroquinone of the formula:

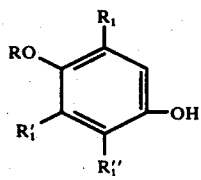
                                                                III wherein $R_1$, $R_1'$ and $R_1''$ are as above;
is converted to a compound of the formula:

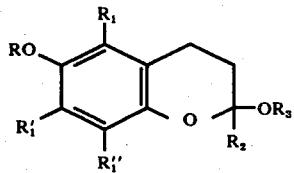
                                                                IV wherein R, $R_1$, $R_1'$, $R_1''$ and $R_2$ are as above; and $R_3$ is lower alkyl.

One method of preparing the compound of formula IV where $R_2$ is methyl, is by reacting the compound of formula III with a compound of the formula:

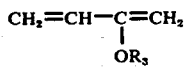
                                                                V-A wherein $R_3$ is as above.

This reaction is carried out at a temperature of 120° C. to 250° C. In carrying out this reaction, pressures of from atmospheric to 1,000 p.s.i. gauge can be utilized. This reaction takes place in an inert organic solvent. Any inert organic solvent can be utilized in carrying out this reaction. Among the preferred inert organic solvents are the aromatic hydrocarbon solvents such as toluene, xylene, and benzene, with benzene being especially preferred.

Another method of forming the compound of formula IV is by reacting the compound of forumla III with any one of the following compounds:

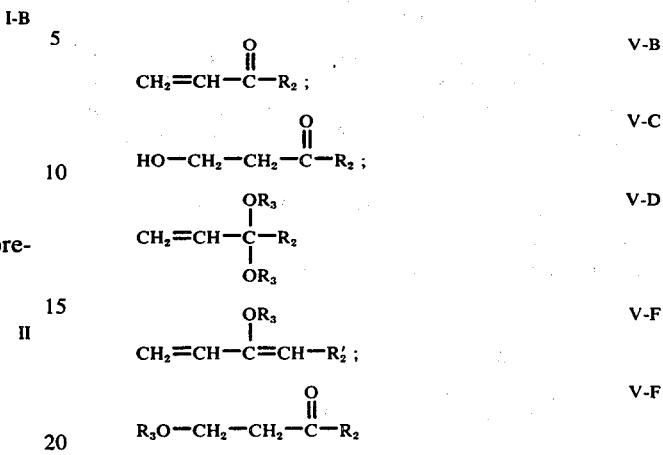

wherein R, $R_2$ and $R_3$ are as above; and $R_2'$ is hydrogen, lower alkyl containing from 1 to 6 carbon atoms or phenyl. The reaction of a compound of formula III with a compound of formula V-E produces a compound of the formula IV where $R_2$ is $-CH_2 R_2'$.

The reaction of a compound of formula III with a compound of the formulae V-B through V-F is carried out in the presence of an acid catalyst. Any conventional acid catalyst can be utilized in carrying out this reaction. Among the preferred acid catalysts are the mineral acids such as sulfuric acid, perchloric acid, hydrobromic acid and phosphoric acid, with sulfuric acid being especially preferred. If desired, this reaction can be carried out in the presence of a dehydrating agent. It has been found that through the use of a dehydrating agent, the yield of the compound of formula IV is increased. Any conventional dehydrating agent can be utilized in carrying out this reaction. Among the preferred dehydrating agents arc included tri-lower alkyl orthoformates such as trimethylorthoformate, etc., calcium chloride, sodium sulfate, acetone dimethyl ketal, etc., with trimethylorthoformate being especially preferred. In carrying out this reaction, an organic alcohol such as a lower alkanol is utilized as the solvent. Among the preferred lower alkanols are included methanol, ethanol, isopropanol, etc., with methanol being preferred. However, any conventional alcoholic solvent can be utilized in carrying out this reaction. In this reaction, temperature and pressure are not critical and this reaction can be carried out at room temperature and atmospheric pressure. On the other hand, elevated and reduced temperature can be utilized to carry out this reaction. Generally, temperatures of from −20° C. to the reflux temperature of the reaction medium are utilized.

Where R in the compound of formula IV is hydrogen, the free hydroxy group can, if desired, be protected by esterification to provide an ester protecting group removable by hydrolysis or by etherification to provide an ether protecting group removable by hydrogenolysis or hydrolysis. Any conventional ester protecting group removable by hydrolysis can be used to protect the hydroxy group. On the other hand, any ether group removable by hydrogenolysis or hydrolysis can be used to protect the hydroxy group. Any conventional method of esterification or etherification can be utilized to protect the free hydroxy group formed by -OR in the compound of formula IV. Among the preferred methods of esterification is to react the compound of formula IV with a reactive derivative of an organic acid such as an acid chloride or acid anhydride. Any of the conditions conventional in carrying out these reactions can be utilized. The preferred esters of compounds of formula IV are the lower alkanoic acid esters of the compound of formula IV with the acetate esters being especially preferred. In converting the hydroxy group to an ether moiety, any conventional method of etherification can be utilized. The preferred group for use in this reaction is the benzyl ether.

The compound of formula IV either having a free hydroxy group or its hydroxy group protected by esterification or etherification is next hydrolyzed with mineral acid to produce a compound of the formula:

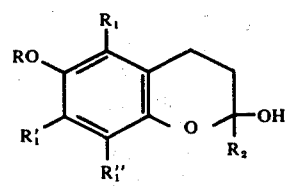

II wherein R, $R_1$, $R_1'$, $R_1''$ and $R_2$ are as above. Any conventional method of acid hydrolysis such as utilizing strong mineral acids which include sulfuric acid, hydrochloric acid, etc., can be utilized in this conversion. Where the hydroxy group in the compound of formula II has been etherified, strong acid treatment may hydrolyze this ether group to form the corresponding hydroxy group.

The compound of formula II is converted to the compound of formula I-A by the following reaction scheme:

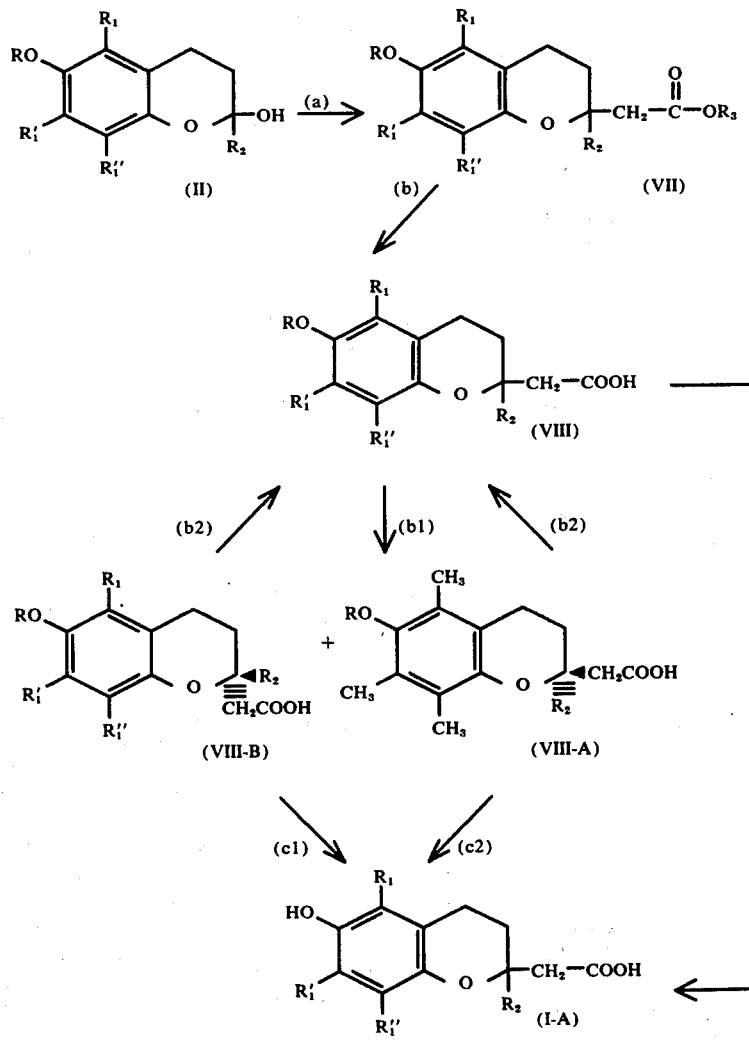

wherein R, $R_1$, $R_1'$, $R_1''$, $R_2$ and $R_3$ are as above.

The reaction of step (a) is carried out with a phosphorane of the formula:

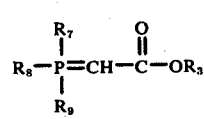

X wherein $R_3$ is as above; $R_7$, $R_8$ and $R_9$ are aryl; or a phosphonate of the formula:

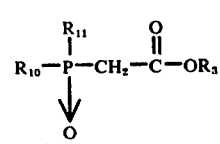

X-A wherein $R_{10}$ and $R_{11}$ are aryloxy or lower alkoxy and $R_3$ is as above.

In accordance with the process of this invention, it has been discovered that a Wittig type reaction utilizing the compound X or a Horner type reaction utilizing the compound of formula X-A can be carried out on a 2-hydroxy substituted chroman nucleus such as present in the compound of formula VI. By utilizing this step to prepare a compound of formula VII, the procedure of this invention avoids any ozonation reaction and the deleterious effects of ozonizing on a chroman nucleus.

The reaction of a phosphorane of formula X with the compound of formula II can, if desired, be carried out in the presence of an organic solvent. In carrying out this reaction, any conventional organic solvent can be utilized. Among the conventional organic solvents which can be utilized in accordance with this invention are included benzene, toluene, N,N-dimethylformamide, 1,2-dimethoxyethane, tetrahydrofuran and dioxane. In carrying out this reaction, temperature and pressure are not critical, and this reaction can be carried out at from about 0° C. to about 50° C. and at atmospheric pressure.

The phosphoranes of formula X above can be prepared by known procedures from the corresponding phosphonium salts. In accordance with this invention, $R_7$, $R_8$ and $R_9$ can be an aryl group. The aryl groups which may form the substituent designated by $R_7$, $R_8$ and $R_9$ include mononuclear aryl groups such as phenyl or substituted phenyl such as tolyl, xylyl, mesityl, 4-methoxyphenyl, etc. The aryl substituent can be a polynuclear aryl group such as naphthyl, anthryl, phenanthryl, etc.

The reaction between the phosphonate of formula X-A and the compound of formula VI can be carried out by first providing a solution of an alkali metal base and the phosphonate of formula X-A in an inert organic solvent and then adding the compound of formula II to this reaction mixture. In carrying out this reaction, any conventional alkali metal base can be utilized such as the alkali metal hydrides such as sodium hydride and alkyl lithium; alkali metal lower alkoxides such as sodium methoxide and sodium ethoxide; and the alkali metal amide bases such as sodamide, potassium amide, as well as other alkali metal lower alkyl amides. In carrying out this reaction, any conventional inert organic solvent can be utilized such as benzene, toluene, N,N-dimethylformamide, tetrahydrofuran, dioxane, 1,2-dimethoxyethane. In carrying out this reaction, a temperature of from 0° C. to the reflux temperature of the solvent may be utilized.

The phosphonate of formula X-A can be substituted by alkoxy or aryloxy groups. As with $R_7$, $R_8$ and $R_9$ in the phosphorane of formula X, the aryl groups contained in $R_{10}$ and $R_{11}$ in the phosphonate of formula X-A can be mononuclear or polynuclear aryl groups which may be substituted or unsubstituted. When the compound of formula X-A is substituted by alkoxy groups, it is generally preferred to utilize alkoxy groups containing from 1 to 4 carbon atoms such as methoxy, ethoxy and isopropoxy. Among the aryloxy groups, phenoxy groups which are unsubstituted are generally preferred.

Where R in the compound of formula II is a hydrolyzable ester group, the reaction of step (a) via the phosphonate of formula X-A may produce a compound of formula VII where R is a hydrogen. The free hydroxy group in the compound of formula VII can, if desired, be re-esterified, to form a hydrolyzable ester group.

The compound of formula VII is converted, via reaction step (b), to the compound of formula VIII. Any conventional means of basic hydrolysis can be utilized to carry out the reaction of step (b). Generally, the reaction of step (b) can be carried out in an aqueous medium utilizing an alkali metal hydroxide such as sodium hydroxide. In carrying out this reaction, temperatures of from about 5° C. to the reflux temperature of the reaction medium are utilized. This basic hydrolysis converts the hydrolyzable ester group R in the compound of formula VII to the hydrogen moiety in the compound of formula VIII. Where R in the compound of formula VIII is a hydrogen, the hydroxy group formed thereby can be esterified by conventional means to form the compound of formula VIII where R forms a hydrolyzable ester protecting group.

The compound of formula VIII can be separated into its enantiomers by any conventional chemical means. Among the preferred chemical means is to react the compound of formula VIII with an optically active base. Any conventional optically active base can be utilized to carry out this resolution. Among the preferred optically active bases are the optically active amine bases such as alpha-methylbenzylamine, quinine, dehydroabietylamine and alpha-methylnaphthylamine. Any of the conventional techniques utilized in resolving organic acids with optically active organic amine bases can be utilized in carrying out this reaction.

In the resolution step, the compound of formula VIII is reacted with the optically active base in an inert organic solvent medium to produce salts of the optically active amine with both the 2R and 2S isomers of the compound of formula VIII. In the formation of these salts, temperatures and pressure are not critical and the salt formation can take place at room temperature and atmospheric pressure. On the other hand, higher or lower temperatures can be utilized. In carrying out this salt formation, any conventional inert organic solvent can be utilized. The R and S salts can be separated by any conventional method such as fractional crystallization. After crystallization, each of the salts can be converted to the respective compounds of formula VIII-A and formula VIII-B by hydrolysis with an acid. Any conventional method of hydrolysis with an acid can be utilized to hydrolyze these salts. Among the preferred acids are dilute aqueous mineral acids, i.e., from about 0.001N to 2N aqueous acids, such as aqueous sulfuric acid or aqueous hydrochloric acid.

The reaction of step (b1) produces the compound of formula VIII in its 2S form (the compound of formula VIII-A) and in its 2R form (the compound of formula VIII-B). If one wishes to prepare natural tocopherol, one utilizes the compound of formula VIII-A in the rest of the synthesis disclosed hereinafter. On the other hand, if one wants to prepare other isomers of natural alpha-tocopherol, the compound of formulae VIII-B or VIII is utilized in the rest of this process.

On the other hand, in accordance with this invention, either the compound of the formula VIII-A or formula VIII-B can be converted to the compound of formula VIII via reaction step (b2). By means of this step, one can take the isomer of formula VIII which does not lead to natural alpha-tocopherol and racemize it back to the compound of the formula VIII. Alternatively, one can take the natural isomer, i.e., the compound of formula VIII-A and racemize it back to the compound of formula VIII. Hence, by this method, the yield of the compound of formula VIII-A (the compound which leads to natural alpha-tocopherol) or of the compound of formula VIII-B can be substantially increased. Therefore, the process of this invention provides a method for producing the natural alpha-tocopherol as well as other isomers of alpha-tocopherol in high yields.

The reaction of the compound of formula VIII-A or formula VIII-B to form the compound of formula VIII can be carried out by any one of the two procedures. Where R in the compound of formula VIII-A or formula VIII-B is hydrogen or forms an ester group, the compound of formulae VIII-A or VIII-B is converted to the compound of formula VIII by treatment with an aqueous mineral acid. Generally, from 2N to 18N aqueous mineral acid is used. This reaction can be carried out in an aqueous medium. In carrying out this reaction, any conventional mineral acid can be utilized. Among the preferred mineral acids are sulfuric acid, hydrochloric acid, hydrobromic acid, etc. On the other hand, where R is an ether group, the reaction of step (b2) is carried out in the presence of an acid or a strong base. Where the reaction is carried out in the presence of an acid, it is carried out in the same manner described in connection with the racemization of the compound of formulae VIII-A or VIII-B where R is hydrogen. Where the reaction is carried out in the presence of a strong base, the reaction is carried out under anhydrous conditions in the presence of an inert organic solvent. Any conventional inert organic solvent can be utilized to carry out this racemization. Among the preferred inert organic solvents for use in carrying out this racemization are toluene, dioxane, glyme, diglyme, tetrahydrofuran, etc. In carrying out this reaction, any conventional strong alkali metal base can be utilized. Among the strong bases are the alkali metal hydrides such as sodium hydride and the alkali metal dilower alkyl amides. Among the preferred alkali metal dilower alkyl amides are lithium diisopropyl amide and lithium isopropylcyclohexyl amide. In carrying out this racemization in the presence of an acid or a base temperature and pressure are not critical and this reaction can be carried out at room temperature and atmospheric pressure. On the other hand, higher or lower temperatures can be utilized. Generally, it is preferred to utilize a temperature of from 20° C. to the reflux temperature of the reaction mixture in carrying out this reaction. When R is an ester group in the compound of formulae VIII-A and VIII-B, this group may be cleaved to hydrogen during racemization.

Where R forms an ether or ester group in the compound of formulae VIII, VIII-A and VIII-B, these compounds can be converted to the compound of formula I-A by hydrolysis or hydrogenolysis depending wthether R is an ester protecting group removable by hydrolysis or an ether protecting group removable by hydrolysis or hydrogenolysis. Any conventional method of ether or ester hydrolysis or ether hydrogenolysis can be utilized in carrying out this procedure.

The compound of formula VIII where $R_2$ is phenyl or lower alkyl can also be prepared from the compound of formula II where $R_4$ is phenyl or lower alkyl via the following intermediates:

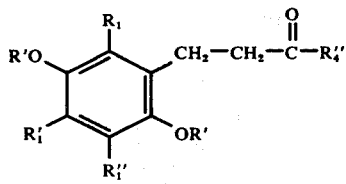

wherein $R_1$, $R_1'$ and $R_1''$ are as above; $R_4''$ is lower alkyl or phenyl and $R'$ forms an ether protecting group removable by hydrogenolysis or hydrolysis or an ester protecting group removable by hydrolysis; and

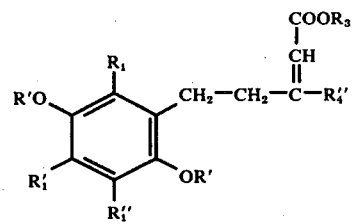

where $R_1$, $R_1'$, $R_1$ , $R'$, $R_4''$ and $R_3$ are as above.

The compound of formula II where $R_4$ is phenyl or lower alkyl is converted to the compound of formula XI by esterification or etherification. Any conventional method of etherification such as those described hereinbefore can be utilized to carry out this reaction. The compound of formula XI is converted to the compound of formula XII by reaction with a compound of formulae X or X-A as described in connection with the reaction of step (a). The compound of formula XII is converted to the compound of formula VII where R is hydrogen and $R_2$ is $R_2'$ by cleavage of the group $R'$. Where $R'$ is an ester, this conversion is carried out by ester hydrolysis. Any conventional method of ester hydrolysis can be utilized to carry out this conversion. On the other hand, where $R'$ is an ether group removable by hydrolysis or hydrogenolysis any conventional method of ether hydrolysis or hydrogenolysis can be utilized to carry out this reaction.

In accordance with another embodiment of this invention, the compound of formula VII can be prepared from a compound of formula II or a compound of the formula XI via the following intermediates:

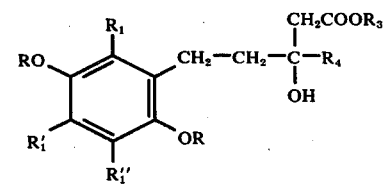

wherein R, $R_1$, $R_1'$, $R_1''$, $R_3$ and $R_4$ are as above; and

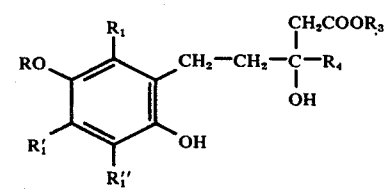

wherein R, $R_1$, $R_1'$, $R_1''$, $R_3$ and $R_4$ are as above

In the preparation of a compound of formula XIII, the compound of formula II above or the compound of formula XI is reacted with either a compound of the formula:

XZnCH₂COOR₃      XV-A wherein X is halo and R₃ is as above; or

LiCH₂COOR₃      XV-B wherein R₃ is as above.

The reaction of the compound of formulae II or XI with the compound of the formula XV-A to produce a compound of the formula XIII is carried out via a Reformatsky reaction. Any of the conditions conventional in Reformatsky reactions can be utilized in carrying out this reaction. On the other hand, the reaction of the compound of formula II or the compound of the formula XI with the compound of the formula XV-B to produce a compound of the formula XIII is carried out via the Rathke reaction. This reaction is carried out at a temperature of at most −15° C. Generally, temperatures of about −80° C. to −50° C. are preferred in carrying out this reaction. Furthermore, this reaction is carried out in the presence of an inert organic solvent. Any conventional inert organic solvent which solidifies at a temperature below −50° C. can be utilized in carrying out this reaction. Among the preferred solvents are included tetrahydrofuran and diethyl ether. In carrying out the Rathke or Reformatsky reaction with either the compound of the formulae XV-A or XV-B, the compound of formula II is directly converted to the compound of formula XIV. On the other hand, where the compound of formula XI is utilized the compound of formula XIII is formed as an intermediate. The compound of formula XIII is converted to the compound of formula XIV by hydrolysis or hydrogenolysis depending upon the substituent R. Any of the conventional methods of hydrolysis or hydrogenolysis discussed in connection with the conversion of the compound of formula XII to the compound of formula VII, can be utilized in carrying out this procedure.

The compound of formula XIV is converted to the compound of formula VII by treating the compound of formula XIV with a strong organic acid dehydrating agent in the presence of an inert organic solvent. Any conventional inert organic solvent can be utilized in carrying out this reaction. Among the preferred organic solvents are the hydrocarbon solvents such as benzene, toluene, etc., and the ether solvents such as dioxane. In carrying out this reaction, a strong organic acid dehydrating agent such as p-toluene sulfonic acid can be utilized. This reaction is generally carried out under anhydrous conditions. In carrying out this reaction, temperature and pressure are not critical and this reaction can be carried out at room temperature and atmospheric pressure. On the other hand elevated or reduced temperatures can be utilized.

The compound of formula I-B above is prepared, in accordance with this invention, from a compound of formulae II or XI above. In the first step of this reaction, the compound of formulae II or XI is converted to a compound of the formula:

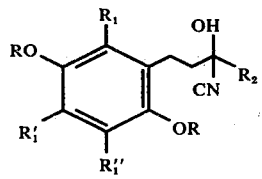

XVII wherein R, R₁, R₁', R₁'' and R₂ are as above. The compound of formulae II or XI is converted to the compound of formula XVII by treating either the compound of formula II or XI with an alkali metal cyanide in an inert organic solvent medium and then maintaining the reaction mixture at a pH of from 3 to 7, preferably from 4 to 6. In carrying out this reaction, the preferred alkali metal cyanide is potassium cyanide. In carrying out this reaction, any conventional inert organic solvent can be utilized as the reaction medium. Generally, it is preferred to utilize solvents such as dimethylsulfoxide or dimethylformamide. Any conventional means of maintaining the reaction medium at a pH of from 3 to 7 can be utilized. Generally, this pH is maintained by the means of adding an acid to the reaction medium containing either the compound of formulae II or XI. Any conventional acid which will maintain the reaction medium at a pH of from 3 to 7 can be utilized. Among the preferred acids are included sulfuric acid and hydrochloric acid. In carrying out this reaction, temperatures of from 0° to 40° C. can be utilized.

In the next step of this reaction, the compound of formula XVII is converted to a mixture of compounds of the formulae:

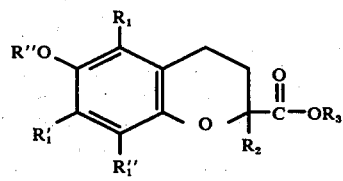

XVIII and

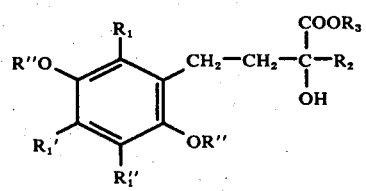

XVIII-A wherein R'' is hydrogen or forms an ether protecting group removable by hydrogenolysis or hydrolysis; and R₁, R₁', R₁'', R₂ and R₃ are as above. This reaction is carried out at a temperature of −20° C. to 10° C. utilizing anhydrous mineral acid in a lower alkanol followed by the addition of water. Any conventional anhydrous mineral acid can be utilized to carry out this reaction. Among the preferred mineral acids are the hydrohalic acids with hydrochloric acid being especially preferred. Any conventional lower alkanol can be utilized in this reaction. Among the preferred lower alkanols are methanol and ethanol.

The mixture of the compounds of formulae XVIII and XVIII-A can be converted to the compound of formula XVIII where R₃ is hydrogen by first hydrolyzing this mixture with base to form a mixture of acids of the formulae:

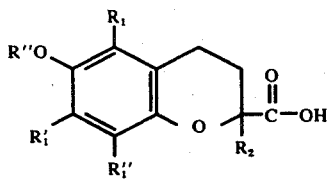

and

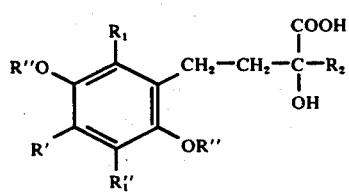

wherein R', R", $R_1$, $R_1'$, $R_1''$ and $R_2$ are as above.

This reaction is carried out by any conventional means of basic hydrolysis. Among the preferred methods is to treat the mixture of compounds of the formulae XVIII and XVIII-A with an alkali metal hydroxide.

The mixture containing compounds of formulae XIX and XIX-A can be converted to the single compound of formula XIX by treating this mixture with a strong organic acid dehydrating agent in the presence of an inert organic solvent. Any conventional inert organic solvent can be utilized in carrying out this reaction. Among the preferred organic solvents are the hydrocarbon solvents such as benzene, toluene, etc., and ether solvents such as dioxane. In carrying out this reaction, a strong organic acid dehydrating agent such as p-toluenesulfonic acid or sulfuric acid can be utilized. This reaction is carried out under anhydrous conditions. If R" in the compound of formula XIX is a hydroxy group, this compound can, if desired, be esterified or etherified by conventional means to produce a compound of formula XIX where R is hydrogen or forms an ester or ether group, i.e., the compound of the formula:

wherein R, $R_1$, $R_1'$, $R_1''$ and $R_2$ are as above.

On the other hand, the compound of formula XVII where R is a hydrolyzable ester group or hydrogen can be directly converted to a compound of formula XX by treating the compound of formula XVII with a strong inorganic aqueous acid in an aqueous medium. In carrying out this reaction where R in the compound of formula XVII is a hydrolyzable ester group, this treatment will cleave the ester group so that R will be hydrogen. In carrying out this reaction, temperature and pressure are not critical and this reaction can be carried out at room temperature and atmospheric pressure. On the other hand, elevated temperatures can be utilized. Any conventional inorganic acid can be utilized to carry out this conversion. Among the preferred acids are concentrated inorganic aqueous acids, i.e., acid having a concentration of at least 12N. Among the preferred acids are sulfuric acid and hydrohalic acids such as hydrochloride acid.

If desired, the compound of formula XX can be resolved, if desired, and converted to the compound of formula I-B according to the following procedure:

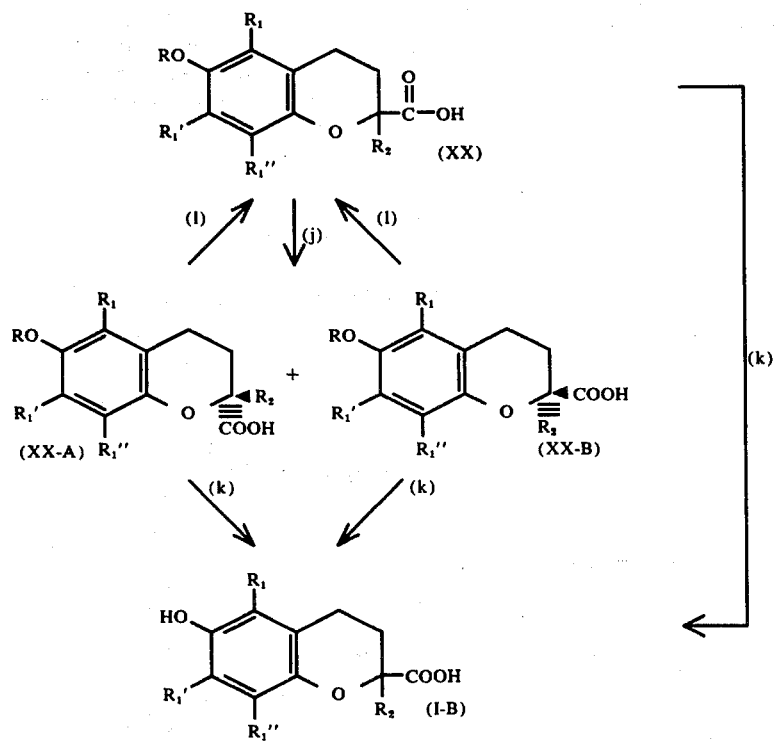

wherein R, $R_1$, $R_1'$, $R_1''$ and $R_2$ are as above.

If desired, the compound of formula XX can be converted, via reaction step (j), into its enantiomers, i.e., the compound of formula XX-A and formula XX-B. The same method of separation as described in connection with step (b1) can be utilized to carry out the resolution of the compound of formula XX. The preferred resolving agent for use in this reaction is an optically active organic amine base such as alpha-methylbenzylamine. As in step (b1), the organic amine base forms salts with both the 2R and 2S isomers of the formula XX which can be separated by conventional methods such as fractional crystallization and hydrolyzed to their respective 2R and 2S isomeric forms as in step (b1). The enantiomer of formula XX-B can be utilized to prepare natural optically active alpha-tocopherol. In accordance with this invention, the same configuration at the 2-position in the compound of formula XX-B is maintained during its conversion to vitamin E compounds. Therefore, the compounds of formula XX-B can be utilized to produce the 2R isomers of the vitamin E compounds. On the other hand, the compound of formula XX-A can be utilized to prepare the 2S isomers of alpha-tocopherol. If desired, the compounds of formula XX-A or XX-B can be racemized to produce the compound of formula XX. This racemization is carried out in the same manner as described in connection with reaction step (b2). This recemization allows the natural isomer precursor XX-B or the unnatural isomer precursor XX-A to be produced in higher yields. On the other hand, the compound of formula XX can be utilized as a precursor for producing the 2RS isomers of vitamin E compounds.

The compound of formulae Xx, XX-A, and XX-B can be converted to the formula I-B by hydrogenolysis, ester hydrolysis or ether hydrolysis utilizing conventional methods for carrying out this hydrolysis or hydrogenolysis such as those described hereinbefore.

The compound of formula XX can also be prepared from the compound of formula III, in accordance with another embodiment of this invention, via the following intermediates:

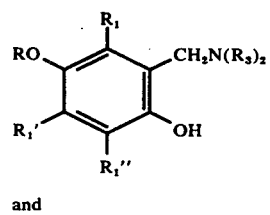   XXI and

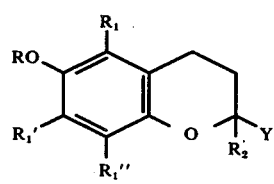   XXII wherein R, $R_1$, $R_1'$, $R_1''$, $R_2$ and $R_3$ are as above; and Y is $-C \equiv N$ or

$-COR_3$.

In accordance with this invention, the compound of formula III is reacted, via a Mannich Reaction, with formaldehyde and an amine of the formula:

$(R_3)_2HN$   XXIII wherein $R_3$ is as above;

to produce the compound of the formula XXI. This reaction is carried out utilizing the conditions conventional in Mannich Reactions. In carrying out this reaction, temperatures of from 0° to 60° C. are generally utilized. Generally, this reaction is carried out in an inert organic solvent. Any conventional inert organic solvent can be utilized with solvents such as methanol and benzene being preferred.

The compound of formula XXI is converted to a compound of the formula XXII by reaction with a compound of the formula:

$$CH_2=C-Y \quad\quad XXIII-B$$
$$\phantom{CH_2=C-}R_2$$

wherein $R_2$ an Y are as above. This reaction is carried out under pressures at a temperature of from 130° C. to 250° C. Generally, this reaction is carried out by heating the compound of formula XXII with the compound of formula XXIII-B in a sealed vessel so that the reaction is carried out under pressure. In carrying out this reaction, the compound of formula XXI can be present in the form of its free base or as an acid addition salt such as a hydrohalic acid addition salt.

The compound of formula XXII is converted to the compound of formula XX by either acid or basic hydrolysis. Any conventional method of acid or basic hydrolysis can be used in carrying out this procedure. If in the compound of formula XXII, R is a protecting group, it is best to utilize the hydrolysis technique that will remove the protecting group so as to obtain a compound of formula I-B directly.

In accordance with another embodiment of this invention, the compound of formula III is converted to a compound of formula I via the following intermediates:

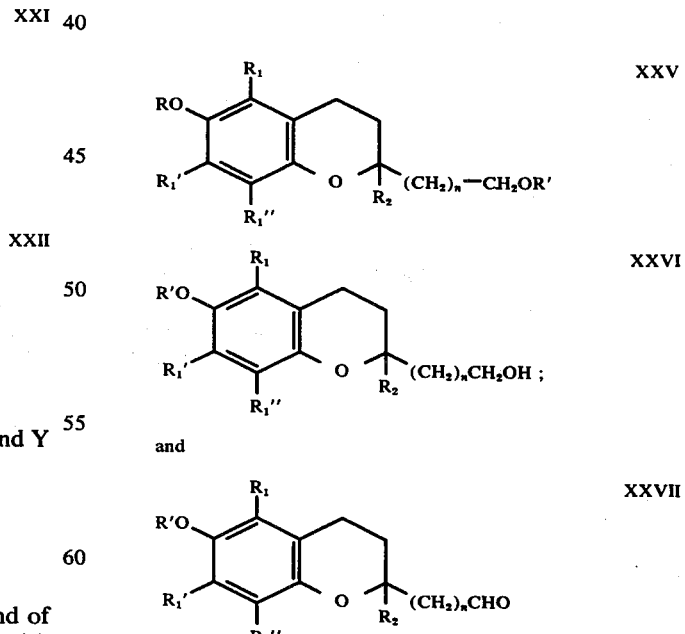

wherein R, R'', $R_1$, $R_1''$, $R_2$ and n are as above.

In the first step of this process, the compound of the formula III is reacted with a compound of the formula:

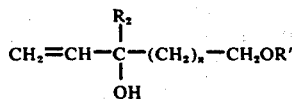

XXIX wherein $R_2$ and $R'$ are as above.

Reaction of the compound of formula III with the compound of the formula XXIX is carried out in the presence of an acid catalyst such as Lewis acid or mineral acid or both. In carrying out this reaction, any conventional Lewis acid or mineral acid can be utilized. Among the conventional Lewis acids which can be utilized are included aluminum trichloride, boron trifluoride, zinc chloride, etc. On the other hand, a mineral acid can be utilized in carrying out this reaction. Among the preferred mineral acids are the hydrohalic acids such as hydrochloric acid, etc. If desired, a mixture of a Lewis and a mineral acid can be utilized in carrying out this reaction. The preferred catalyst system for use in this reaction consists of a mixture of zinc chloride and hydrochlroic acid. In carrying out this reaction, any conventional inert organic solvents can be utilized. Furthermore, this reaction is carried out at a temperature of from −20° C. to the reflux temperature of the reaction mixture.

The compound of formula XXV where R' forms protecting ether and ester groups can be hydrolyzed to form the compound of formula XXVI. Generally, it is preferred to prepare a compound of formula XXV so that R is an ether protecting group, and R' is an ester protecting group or vice-versa. In this manner, hydrolysis of R' will not effect the hydrolysis of R. On the other hand, if R in the compound of formula XXV is hydrogen, the free hydroxy group formed thereby should be protected so that, in the compound of formula XXVI, the phenolic hydroxy group is protected whereas the hydroxy group on this side chain remains free.

The compound of formula XXVI is converted to the compound of formula XXVII by oxidation with silver carbonate ($Ag_2CO_3$), a chromium trioxide-pyridine complex (Collins reagent); chromium trioxide dispersed in a carrier such as graphite (Lalancette reagent); and chromium trioxide in pyridine (Sarett reagent). When silver carbonate is utilized as an oxidizing agent, it is generally employed with a carrier. Any conventional carrier can be utilized, with diatomaceous earth being preferred. In carrying out this oxidation, any of the conditions conventional in oxidizing with silver carbonate can be employed. In utilizing the Collins reagent as an oxiding agent, the oxidation is carried out under the conditions conventional in utilizing a Collins reagent such as in a halogenated hydrocarbon solvent, preferably methylene chloride at room temperature, i.e., from about 10° centrigrade to about 30° centrigrade. When utilizing the Lalancette reagent, oxidation is carried out under conditions conventional in utilizing this reagent as an oxidizing agent. Generally, with the Lanancette reagent, oxidation is carried out in an aromatic hydrocarbon solvent such as benzene and toluene under reflux. In utilizing the Sarett reagent, oxidation is carried out under conditions conventional in utilzing such a reagent. It is by utilizing these oxidizing agents in the oxidation of a compound of the formula XXVI to a compound of the formula XXVII, that this reaction is carried out without any destruction of the chroman ring. This is completely surprising since it is well known that chroman rings are very susceptible to oxidation.

The conversion of a compound of the formula XXVII to a compound of the formula I is carried out by utilzing as an oxidizing agent, silver oxide ($Ag_2O$). In carrying out this reaction, any of the conditions conventional in oxidizing with silver oxide can be utilized in carrying out this reaction. Generally, this reaction is carried out in an inert organic solvent. Any conventional inert organic solvent can be utilized. Furthermore, in carrying out this reaction, temperature and pressure are not critical and the oxidation can be carried out at room temperature abd atmospheric pressure. On the other hand, elevated or reduced temperatures can be utilized. The group R can be hydrolyzed to form the free phenolic moiety by conventional means such as decribed hereinbefore.

In accordance with an embodiment of this invention, the compound of formula XXVI where it is a racemate, can be resolved into either its 2R form which has the formula:

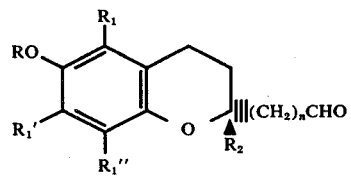

wherein R, $R_1$, $R_1'$, $R_1''$, $R_2$ and n are as above; and its 2S form which has the formula:

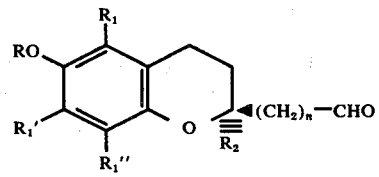

wherein n, R, $R_1$, $R_1'$, $R_1''$ and and $R_2$ are as above.

The compound of formula XXVII where it is in the form of a racemate can be resolved into its optically active anitpode by utilizing any conventional means for resolving aldehydes. Among the methods conventionally employed for resolving aldehydes is reacting the aldehyde with an optically active amine such as alphamethylbenzyl amine or dehydroabietylamine to form a Schiff base. On the other hand, the aldehyde can be reacted with a racemic amine followed by salt formation with an optically active acid. Another method for resolving the aldehyde of formula XXVII is by reacting the aldehyde with an optically active hydrazide to form a hydrazone. Any other conventional optically active amines, racemic amines, optically active acids and optically active hydrazides utilized in resolving aldehydes can be utilized in this process. The diastercomeric mixtures formed by the reaction of the aldehyde with the optically active amine or with the racemic amine followed by salt formation with an optically active acid or the hydrazone formed from the optically active hydrazide can be separated by conventional methods such as crystallization, etc. The optically active aldehyde can be regenerated by standard methods.

If one wants to prepare natural tocopherol, one utilizes the compound of formula XXVII in its S form in the rest of this synthesis. On the other hand, if one wants or prepare other isomers of natural alpha tocopherol, the compound of formula XXVII or the R form can be utilized in the rest of this process. On the other hand, in accordance with this invention, either the compound of R or S form of the compound of formula XXVII can be converted to the racemic form of the compound of formula XXVII by the reaction described hereinbefore in reaction step (b2). By means of this step, one can take the isomer of formula XXVII which does not lead to alpha tocopherol and racemize it back. Alternatively, one can take the natural isomer, i.e., the S form and racemixe it back to the compound of formula XXVII. By this manner, the yield of the compound in the S or R forms of the compound of formula XXVII can be substantially increased.

The compound of formula XXVII can also be prepared from the compound of formula I above the where the phenolic hydroxy is protected with a hydrolyzable ester or an ether group removable by hydrolysis or hydrogenolysis. In this procedure, a compound of the formula:

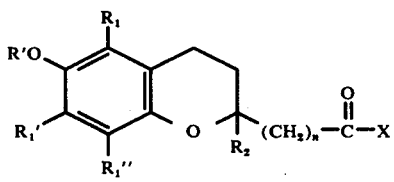

XXX wherein R', R$_1$, R$_1$', R$_1$'', n and R$_2$ are as above; and X is a halogen;
is formed as an intermediate. The compound of formula XXX can be formed from the compound of formula I having its phenolic hydroxy group protected by utilizing conventional methods for converting a carboxylic acid to the corresponding acid halide. Any method conventional in halogenating acids can be utilized in carrying out this reaction. Among the preferred methods of halogenating the compound of formula I is by treating this compound with a halogenating agent, preferably a chlorinating agent such as oxalyl chloride, thionyl chloride, phosphorous pentachloride, etc. Any conventional halogenating agent can be utilized in carrying out this reaction.

The compound of formula XXX is converted to the compound of formula XXVII by Rosenmund reduction. Any of the conditions conventional in Rosenmund reduction can be utilized in carrying out this reaction. Generally, this reaction is carried out by hydrogenation in the presence of a deactivated palladium catalyst and acid acceptor. Any of the conventional deactivated palladium catalyst such as palladium containing an organic sulfur derivative or quinoline such as is conventional in the art can be utilized in this reaction. Any conventional acid acceptor such as a base can be utilized in carrying out this reaction. Among the preferred bases are alkali metal salts of lower alkanoic acids such as sodium acetate, and tri-lower alkylamines such as triethylamine, etc. If R is an ether protecting group removable by hydrogenolysis, this reaction may remove the ether group to produce the compound of formula XXVII where R is hydrogen. However, where-OR forms a benzyl ether moiety which is susceptible to hydrogenolysis, this reaction will unexpectedly selectively reduce the acid chloride without affecting the benzyl ether moiety.

Another method for forming the compound of formula XXVII is by reducing compounds of formulae VII or XXII where R forms a hydroxy protecting group. This reduction can be carried out by treating the compound of formula VII or formula XXII with diisobutyl aluminum hydride or sodium dihydro-bis-(2-methyoxyethoxy)-aluminum hydride as a reducing agent. This reduction is carried out in an inert organic solvent medium. Any conventional inert organic. solvent can be utilized in carrying out this reaction. Among the preferred inert organic solvents are included pentane, dioxane, diethyl ether, hexane, toluene, benzene or xylene. Generally, temperatures of from −120° C. to −30° C. are utilized in carrying out this reaction.

In accordance with this invention, the compound of formula XXVII either in its 2R or 2S form, where R', R$_1$', R$_1$'' and R$_2$ are all methyl, a compound of the formula:

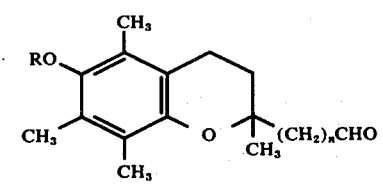

XXVII-A wherein n and R are as above;
can be converted to a vitamin E active compound of the formula:

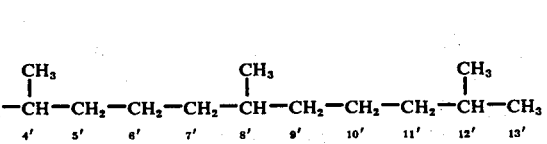

XL wherein R is as above.

Beside producing the natural optically active compound of formula XL having the 2R', 4'R and 8'R configuration, this synthesis can be utilized to produce compounds of the formula XL havng the following stereo configuration:
2R, 4'RS, 8'RS;
2S, 4'R, 8'R;
2S, 4'RS, 8'RS;
2RS, 4'RS, 8'RS; and
2RS, 4'R, 8'R.

The compound of formula XXVII-A forms compounds having the following formula:

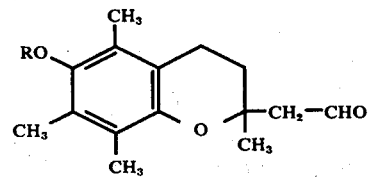

XXVII-B and

-continued

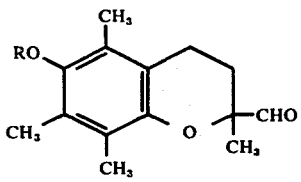

XXVII-C

Where it is desired to produce the compound of formula XL in the following isometic forms:
2R, 4'RS, 8'RS;
2S, 4'RS, 8'RS; and
2RS, 4'RS, 8'RS.
The compound of formula XXVII-B is reacted with a 2RS, 6RS isomer selected from the group consisting of a phosphorane of the formula:

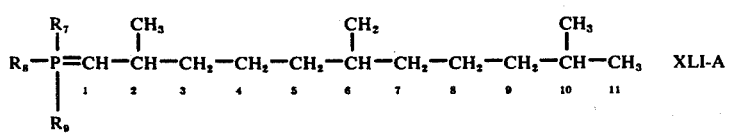

wherein $R_7$, $R_8$ and $R_9$ are as above;
and a phosphonate of the formula:

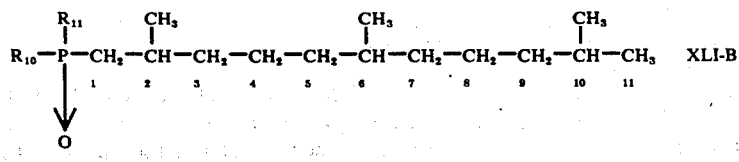

wherein $R_{10}$ and $R_{11}$ are as above;
to produce a compound of the formula:

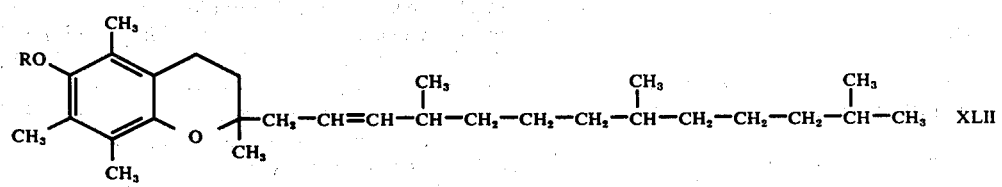

wherein R is as above.

Where the compound of formula XXVII-B is in its 2R form, the reaction of the compound of formula XXVII-B with the compound of the formula XLI-A or formula XLI-B produces the compound of formula XLII in its 2S, 4'RS, 8'RS form. On ther other hand, where the compound of formula XXVII-B is in its 2S form, the reactions of the compound of the formula XXVII-B with the compond of the formula XLI-A or the formula XLI-B produces the compound of formula XLII in its 2R, 4'RS, 8'RS form. However, if the compound of formula XXVII-B is a 2RS isomeric mixture, this reaction produces a compound of formula XLII having the 2RS, 4'RS, 8'RS form.

The reaction of the compound of formula XXVII-B with a compound of formula XLI-A or XLI-B is carried out in the same manner as described in connection with the reaction of the compounds of formulae X or X-A with the compound of formula II. Where the compound of the formula XXVII-B contains a hydrolyzable ester group, this reaction may cause hydrolysis to the corresponding hydroxy group. If desired, this hydroxy group of the compound of formula XLII can be etherified or re-esterified in the manner described hereinbefore.

The compound of formula XLII can be converted to the compound of formula XL by hydrogenation. Any conventional method of hydrogenation can be utilized in carrying out this reaction. Generally, it is preferred to carry out this reaction by hydrogenating the compound of formula XLII in the presence of a noble metal catalyst such as palladium or platinum. While palladium or platinum is preferred, any conventional noble metal catalyst can be utilized to carry out this reaction.

Any of the common supports for the noble metal catalyst can be utilized in accordance with this invention.

Among the preferred catalyst supports for use in this invention are such supports as carbon, barium sulfate, etc. In carrying out this hydrogenation reaction, any of the conventional inert organic solvents can be utilized. In carrying out this reaction, temperature and pressure are not critical and this reaction can be carried out at room temperature and atmospheric pressure. On the other hand, higher or lower temperatures and pressures can be utilized. Where R in the compound of formula XLII is an ether group removable by hydrogenolysis, this hydrogentation will cleave the ether group to produce a compound of formula XL where R is H. The resulting hydroxy group in the compound of formula XL can, if desired, be etherified or esterified.

The compound of formula XLI-A and formula XLI-B are prepared from the known 2RS, 6RS isomer of compounds of the formula:

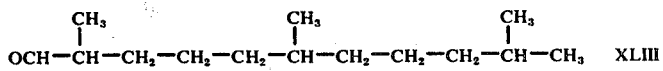

via the following reaction scheme:

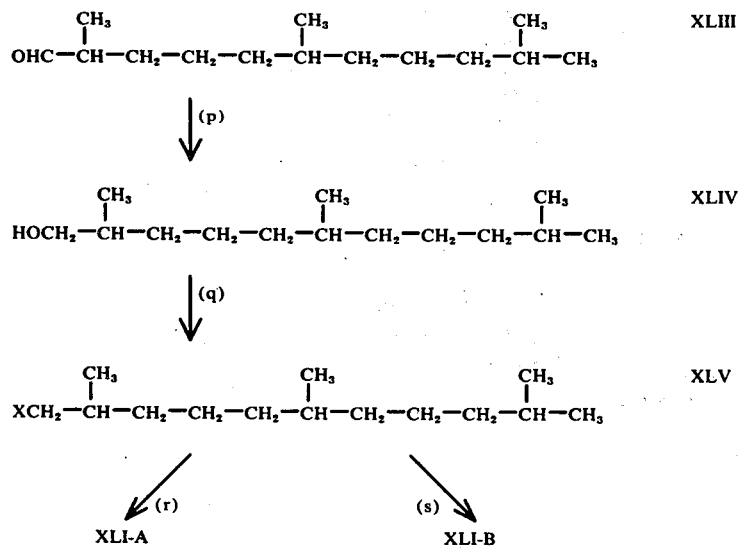

The compound of formula XLIII is converted to the compound of formula XLIV by treating the compound of the formula XLIII with a reducing agent. Any conventional reducing agent capable of converting an aldehyde to the corresponding alcohol can be utilized. Among the conventional reducing agents are the metal hydride reducing agents. Any conventional metal hydride reducing agent can be utilized to carry out this reaction. The compound of formula XLIV is converted to the compound of formula XLV via reaction step (q) by halogenation. Any conventional method of halogenating an alcohol can be utilized in carrying out reaction step (q). Generally, the halogenation can be carried out by treating the compound of formula XLIV with a halogenating agent such as hydrogen bromide gas or phosphorous tribromide. Any of the conditions conventional in halogenating alcohols through the use of halogenating agents can be utlized in carrying out this procedure.

The phohsphorane of formula XLI-A is prepared via reaction step (r) by reacting the compound of formula XLV with a phosphine of the formula:

$$R_8-\underset{\underset{R_9}{|}}{\overset{\overset{R_7}{|}}{P}}$$

wherein $R_7$, $R_8$ are as above.

This reaction is carried out utilizing the procedure well known and conventional in the art for preparing phosphoranes from phosphines. Generally, this reaction is carried out at temperatures of form 80° C. to 250° C. in the presence or absence of an inert organic solvent which has a boiling point above 80° C. Heating phosphine with the compound of formula XLV in this manner produces the phosphonium salt of the compound of formula XLI-A. This phosphonium salt is converted to the compound of formula XLI-A by treatment with a base. Any of the conventional bases utilized in preparing phosphoranes can be utilized in this reaction. Among the preferred bases are alkali metal hydrides, alkali metal lower alkoxides or alkali metal hydroxides. Any of the conditions conventional in forming a phosphorane from its corresponding phosphonium salt can be utilized in carrying out this reaction.

The compound of formula XLI-B is formed, via rection steps (s), by reacting the compound of formula XLV with a phosphite of the formula:

$$R_{12}-\underset{\underset{R_{10}}{|}}{\overset{\overset{R_{11}}{|}}{P}}$$

wherein $R_{10}$ and $R_{11}$ are as above: and $R_{12}$ is lower alkoxy or aryloxy. Any of the conventional methods of forming phosphonates can be used in carrying out the reaction of step (s). Among the methods for forming the phosphonates of formula XLV-B is by heating the phosphite and the compound of formula XLV to a temperature of from 80° C. to 150° C. in an inert organic solvent medium. Any conventional inert organic solvent having a boiling point of at least 80° C. can be utilized in carrying out this reaction. Generally, it is preferred to carry out this reaction at the reflux temperature of the reaction medium.

The compound of formula XL can be produced in the following isomeric forms:
2R, 4'RS, 8'RS;
2S, 4'RS, 8'RS; and
2RS, 4'RS, 8'RS.
by first reacting the compound of the formula XXVII-C with a 2RS, 6RS isomeric phosphorane of formula:

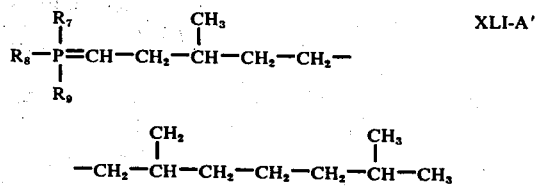

XLI-A' wherein $R_7$, $R_8$ and $R_9$ are as above; and a phosphonate of the formula:

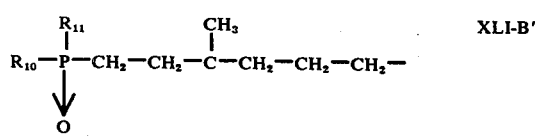

XLI-B'

-continued

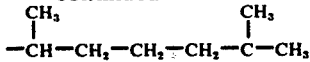

wherein $R_{10}$ and $R_{11}$ are as above;
to produce a compound of the formula:

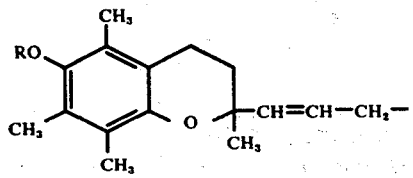  XLII-A

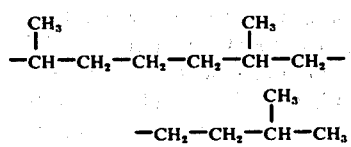

wherein R is as above.

The reaction of compounds of formulae XLI-A' and XLI-B' with the compound of formula XXVII-C to produce the compound of XLII-A is carried out in the same manner as described in connection with the reaction of a compound of the formulae XLI-A and XLI-B with a compound of the formula XXVII-B. The compound of formula XLII-A is converted to the compound of formula XL in the same manner as described in connection with the conversion of a compound of the formula XLII to the compound of formula XL.

The compound of formula XL having the following isomeric forms:
2RS, 4'R, 8'R;
2S, 4'R, 8'R; and
2R, 4'R, 8'R can be prepared in two ways. In the first, the compound of formula XXVII-B above is reacted in the manner described hereinbefore with a phosphorane of the formula:

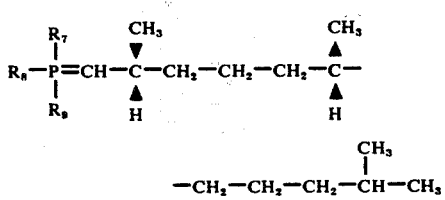  XLV-A wherein $R_7$, $R_8$ and $R_9$ are as above;
or a phosphonate of the formula:

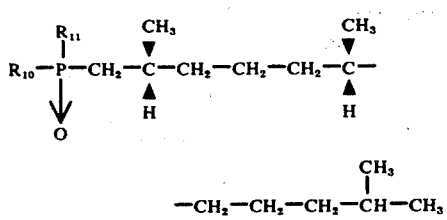  XLV-B wherein $R_{10}$ and $R_{11}$ are as above;
to produce a compound of the formula:

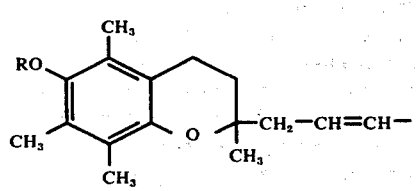  XLII-B

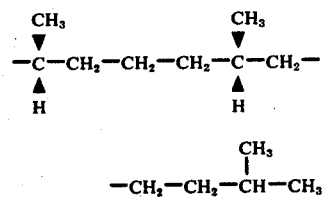

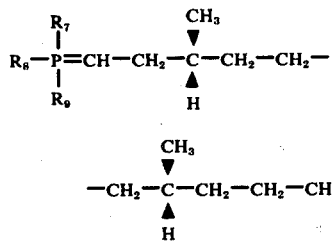

wherein R is as above. In accordance with the second procedure, the compound of formula XXVII-C is reacted with either a phosphorane of the formula:

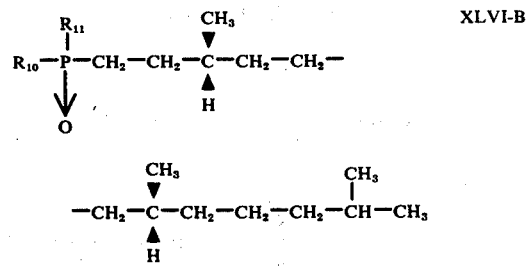  XLVI-A wherein $R_7$, $R_8$ and $R_9$ are as above;
or a phosphonate of the formula:

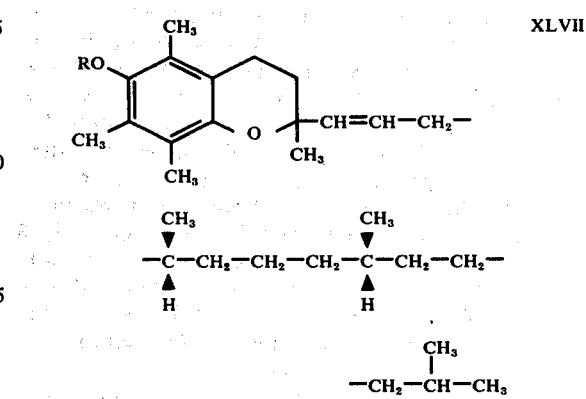  XLVI-B wherein $R_{10}$ and $R_{11}$ are as above; in the manner disclosed hereinbefore to produce a compound of the formula:

XLVII wherein R is as above.

The compound of formulae XLII-B or XLVII can be hydrogenated to form the 4'R, 8'R isomer of formula XL in the same manner as described in connection with the hydrogenation of the compound of formula XLII. If R in the compound of formulae XLII-B or XLVII forms an ether group removable by hydrogenolysis, the hydrogenation step cleaves this ether group of form the compound of formula XL where R is hydrogen. This free hydroxy group in the compound of formula XL can be etherified or esterified. If the compound of formulae XXVII-B or XXVII-C is in the 2R form, then the compound of formula XL produced therefrom will be in the 2S form. On the other hand, where the compound of formulae XXVII-B or XXVII-C in the 2S form, then the compound of formula XL produced therefrom will be in the 2R form. On the other hand, where the compound of formula XXVII-B or the compound of formula XXVII-C is a 2RS isomeric mixture, then the compound of formula XL produced therefrom will be a 2RS isomeric mixture.

The compounds of formulae XLV-A, XLV-B, XLVI-A and XLVI-B can be produced from a compound of the formula:

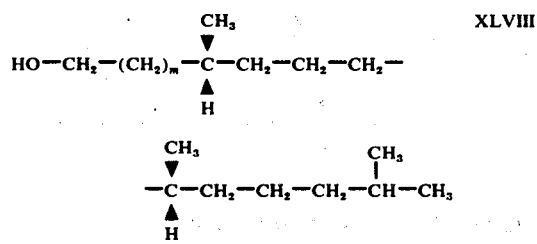

XLVIII wherein m is an integer of from 0 to 1; via an intermediate of the formula:

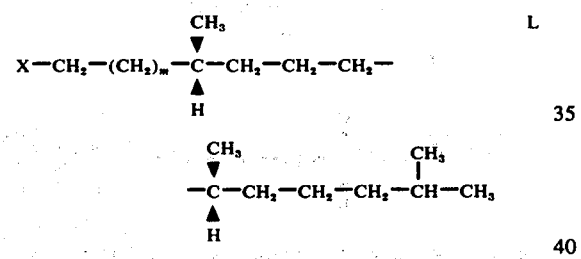

L wherein X and m are as above.

The compound of formula XLVIII is converted to the compounds of formula L utilizing the conditions described in reaction step (q). The compound of formula L can be converted to the compound of formula XLV-A or formula XLVI-A utilizing the conditions described in connection with reaction step (r). When m is 0, this reaction will produce a compound of the formula XLV-A. On the other hand, when m is 1, this reaction will produce a compound of the formula XLVI-A. The compound of formula L is converted to the compound of formula XLV-B or formula XLVI-B utilizing the conditions described in connection with reaction step (s). When m is 0, this reaction will produce a compound of the formula XLV-B. On the other hand, when m is 1,this reaction will produce a compound of the formula XLVI-B.

The compound of formula XLVIII comprises a 2R, 6R isomer which has the formula:

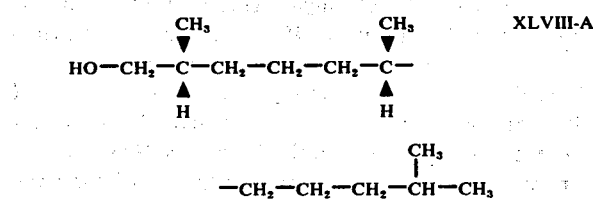

XLVIII-A and a 3R, 7R isomer which has the formula:

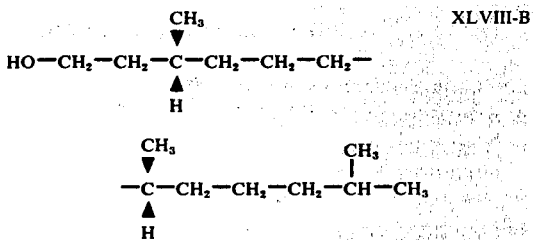

XLVIII-B

The compound of formulae XLVIII-A and XLVIII-B are produced from 7R, 11R-phytol. These compounds are produced from phytol, by dehydrating phytol and then treating the resulting product with ozone gas to form various ozonides, and finally reducing these ozonides with a complex metal hydride. Upon treatment of the ozonide with the complex metal hydride reducing agent a mixture containing the compound of the formula XLVIII-A and a compound of the formula XLVIII-B is formed.

In the first step of this process, phytol is treated with a dehydrating agent in the presence of an inert organic solvent medium. Any of the conditions conventional in dehydrating phytol can be utilized in this reaction step. Any conventional dehydrating agent such as phthalic anhydride, p-toluenesulfonic acid, phosphorous oxychloride and mineral acids such as sulfuric acid can be utilized. Any conventional inert organic solvent or water can be utilized as the dehydrating agent, water is not present in the reaction medium. The use of these conventional dehydrating agents to dehydrate phytol produces a mixture of phytadiene isomers of the formula:

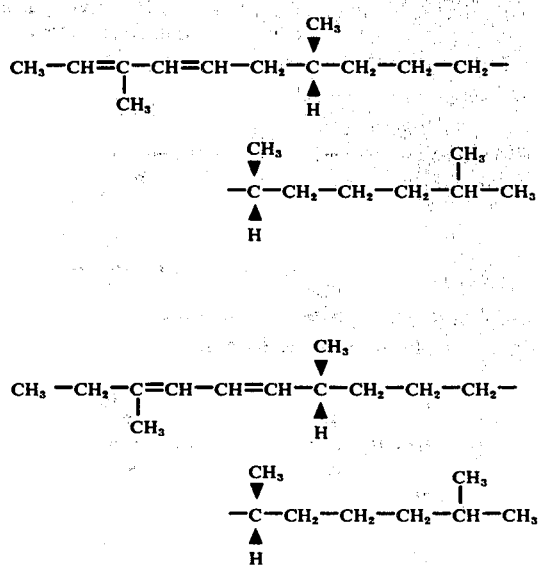

and

This mixture of isomers is subjected to ozone gas in an inert solvent medium to convert the isomers of various structures to their corresponding ozonides. This conversion is carried out by bubbling ozone gas into the reaction medium containing the mixture of isomers, preferably at a temperature of −50° C. to −70° C. In carrying out this step, any conventional inert organic solvent can be utilized. Among the preferred inert organic solvents are the hydrocarbon solvents such as pentane, benzene, toluene, etc., as well as ether solvents such as tetrahydrofuran. The ozonides are then treated with a complex metal hydride reducing agent to form a mixture containing a compound of formulae XLVIII-A and XLVIII-B. Hence, in accordance with this invention, these mixtures of isomers formed from phytol is converted directly to a mixture containing the compound of formula XLVIII-A and the compound of formula XLVIII-B.

This mixture can be separated by fractional distillation. In accordance with this invention, it has been found that the difference between the boiling point of the compound of formula XLVIII-A and formula XLVIII-B are of such magnitude that these compounds can be easily separated by any conventional method of fractional distillation. In carrying out this separation, any conventional means of fractional distillation can be utilized.

The compounds of formula L, either in its 2R, 6R form ($m = 0$) or in its 3R, 7R form ($m = 1$) or as a racemate thereof, can be converted to the compound of formula XL by means of the following reaction scheme:

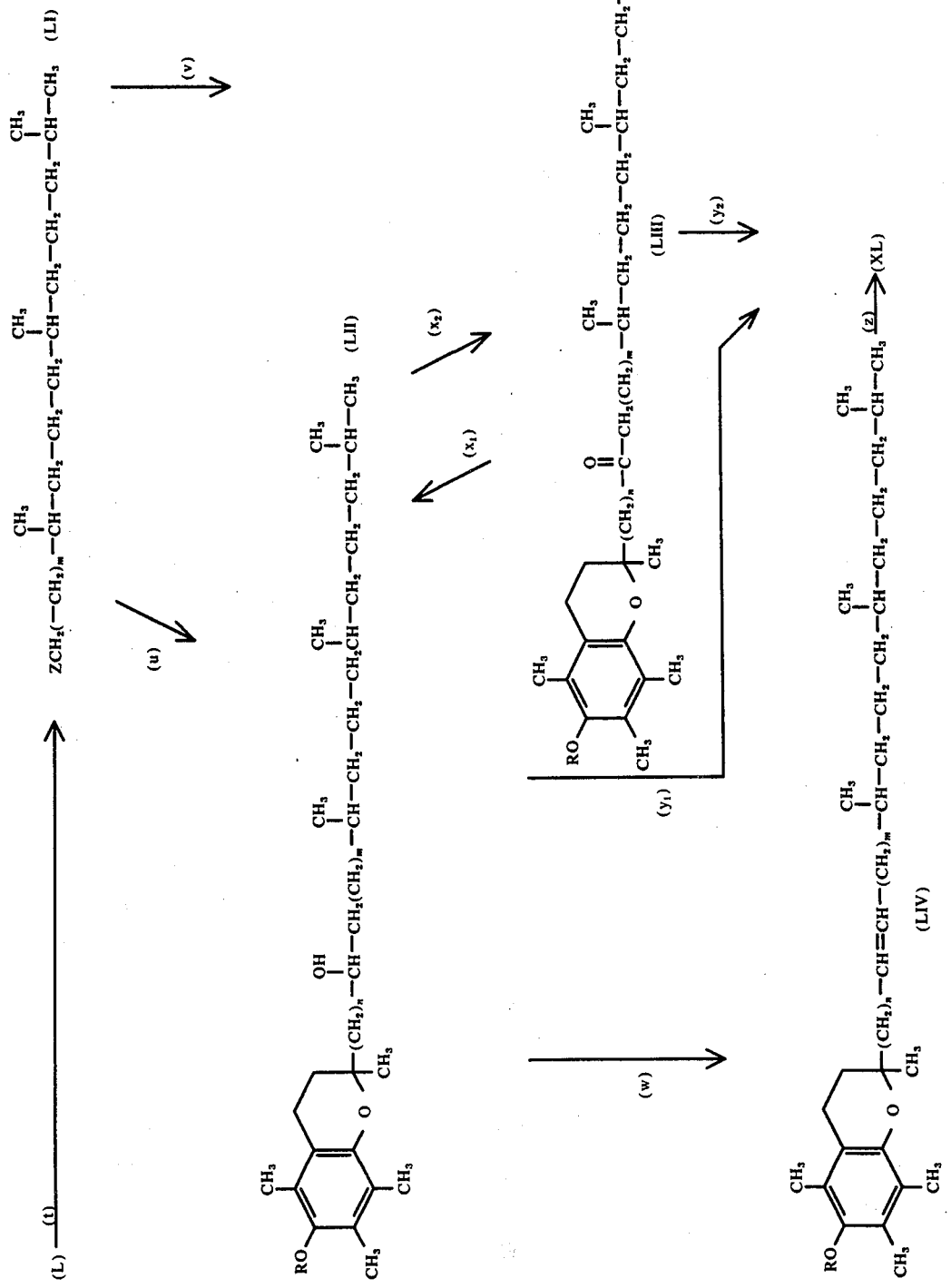

wherein R and X are as above; Z is MgX or Li; and m and n are integers from 0 to 1 with the proviso that the sum of m and n is 1.

The compound of formula L is converted to the compound of formula LI by forming a Grignard salt thereof or an alkyl lithium salt thereof. Any of the conventional methods of forming a Grignard salt or an alkyl lithium salt can be utilized in carrying out the reaction of step (t).

The compound of formula XXX wherein $R_1$, $R_1'$, $R_1''$ and $R_2$ are methyl has the formula:

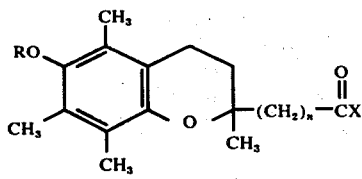

XXX-A wherein R, X and n are as above;
can be converted to the compound of formula XL.

Where the compound of formula XXX-A is utilized as an intermediate in preparing the compound of formula XL and the compound of formula XXX-A has a 2S configuration, the compound of formula XL will have a 2R configuration. On the other hand, if the compound of formula XXX-A has a 2R configuration, the compound of formula XL will have a 2S configuration.

The compound of formula LI is reacted with the compound of formula XXX-A via a conventional coupling reaction to produce the compound of formula LIII. This reaction of step (v) is carried out utilizing standard Grignard conditions. Any conventional standard Grignard conditions can be utilized to carry out this coupling reaction. On the other hand, the compound of formula LI can be reacted via reaction step (u) with a compound of formula XXVII-A to produce a compound of formula LII. The reaction of step (u) is a standard Grignard reaction, and any of the conditions conventional in Grignard reactions can be utilized to carry out the reaction of step (u). In carrying out the reaction of step (u), the substituent in n in the compound of formula XXVII-A and the substituent m in the compound of formula XLI should be chosen so that their sum is equal to 1. This is also true with respect to the substituents m and n in the compounds of formulae XXX-A and LI in the reaction of step (v).

The compound of formula LII can be converted to the compound of formula LIII via reaction step ($x_2$) by oxidation in the same manner as described by the conversion of the compounds of the formula XXVI to the compounds of the formula XXVII. In this oxidation, it is necessary to protect the free phenolic hydroxy group in the compound of formula LII where R is hydrogen. Any of the conditions described hereinbefore in connection with the oxidation of the compounds of formula XXVI to a compound of the formula XXVII can be utilized to convert the compound of the formula LII to a compound of the formula LIII.

On the other hand, the compound of the formula LIII can be converted to the compound of formula LII, via reaction step ($x_1$) by reduction with a complex metal hyride reducing agent. The reduction of step ($x_1$) and the reduction of the ozonides from phtyol to produce the compound of formula XLVIII-A and formula XLVIII-B is carried out with conventional complex metal reducing agents. Among the preferred reducing agents are the complex metal hydrides. Any conventional complex metal hydride reducing agent can be utilized in carrying out this reaction. Among the complex metal hydrides that can be utilized are included the alkali metal borohydrides, such as sodium borohydride or lithium borohydride, alkali metal aluminum hydrides, such as lithium aluminum hydride, diisobutyl aluminum hydride, diisopropyl aluminum hydride and sodium dihydro-bis(2-methoxyethoxy-aluminum hydride). This reduction is carried out in an inert organic solvent medium. Any conventional inert organic solvent can be utilized in carrying out this reaction. Among the preferred inert organic solvents are included tetrahydrofuran, dioxane, diethyl ether, hexane, toluene, benzene or xylene. This reaction can be carried out at room temperature, i.e., 20°–30° C. and atmospheric pressure. On the other hand, reduced temperatures are preferred. Generally, this reaction is carried out at a temperature of from −80° C. to about 45° C.

A compound of formula LIII can be directly converted to the compound of formula XL via reaction step ($y_2$) by utilizing any method of completely reducing a ketone. Among the conventional methods for carrying out this reduction are by the Clemmenson or Wolff-Kischner reactions or by alkali metal borohydride reaction of a derivative of formula LIII where the ketone group is converted to a hydrazone. In carrying out the Clemmenson reaction, the compound of formula LIII is treated with zinc in acetic acid. Any of the conditions conventional in carrying out Clemmenson reactions can be utilized in carrying out the reduction of step ($y_2$). If it is desired to utilize a Wolff-Kischner reaction to convert the compound of formula LIII directly to the compound of formula XL, the compound of formula LIII is treated with hydrazone in the presence of a strong base such as sodium hydroxide at a temperature of from 100° C. to 250° C. in the presence of a high boiling solvent. Any of the conditions conventional in carrying out a Wolff-Kischner reaction can be utilized to carry out the reaction of step ($y_2$). On the other hand, the compound of formula LIII can be converted to the compound of formula XL by first converting the free ketone group contained therein to the hydrazone and then treating the compound of formula LIII with an alkali metal borohydride reducing agent. The hydrazone of the ketones of formula LIII are formed in a conventional manner. Any of the conventional methods for forming a hydrazone such as treating the compound of formula LIII with tosylhydrazone can be utilized. The tosylhydrazone of formula LIII is then reacted with an alkali metal borohydride reducing agent such as sodium borohydride to form the compound of formula XL. Any of the conditions conventional in reducing with an alkali metal borohydride reducing agent can be utilized to carry out this reaction.

The compound of formula LII can be directly converted to the compound of formula XL by treating a derivative of the compound of formula LII where the free hydroxy group contained on the side chain is converted to a leaving group with a complex metal hydride in the manner described in connection with the reduction of a compound of the formula LIII to a compound of the formula LII.

The free hydroxy group on the side of the compound of formula LII can be converted by conventional means to a leaving group. Any conventional leaving group can be utilized in this procedure. Among the preferred leaving group formed are lower alkyl sulfonyloxy such as methanesulfonyloxy and arylsulfonyloxy such as p-toluenesulfonyloxy. Any conventional method of converting a hydroxy group to a leaving group can be utilized in this formation.

The compound of formula LII can also be converted to the compound of formula LIV by treating the compound of formula LII with an alcohol dehydrating agent. Any conventional alcohol dehydrating agent can be utilized. Among the preferred alcohol dehydrating agents are included thionyl chloride, phosphorous oxychloride, inorganic acids such as sulfuric acid, hydrogen bromide, hydrogen chloride, etc.; strong organic acids such as p-toluene sulfonic acid, alkylsulfonic acids such as methane sulfonic acid. Generally, this reaction is carried out in an inert organic solvent. Any conventional inert organic solvent can be utilized in carrying out this reaction. Among the preferred inert organic solvents when thionyl chloride and phosphorous oxychloride are utilized, is pyridine. On the other hand, when hydrogen bromide is utilized, methylene chloride or chloroform are the preferred solvents. In carrying out this reaction, temperature and pressure are not critical, and this reaction can be carried out at room temperature and atmospheric pressure. If desired, higher or lower temperatures can be utilized.

On the other hand, the compound of formula LII can be converted to the compound of formula LIV by first converting a compound of the formula LII to a derivative of the compound of formula LII where the hydroxy group on the side chain is esterified and then subjecting this derivative to pyrolysis. The esterification of the derivative of formula LII can be carried out utilizing conventional procedures of esterification. Among the preferred esters are the lower alkanoic acid esters and the benzoic acid esters. The ester derivatives of the compounds of formula LII can be pyrolyzed to simply heating the compound of formula LII to a temperature of from 150°–300° C. This heating step can be carried out with or without an inert organic solvent. If desired, the pyrolysis can be carried out in a conventional high boiling solvent such as decalin.

The compound of formula LIV can be converted to the compound of formula XL by hydrogenation in the same manner as described in connection with the hydrogenation of a compound of formula XLII to a compound of formula XL.

Where R or R' in the reaction described hereinbefore are ether protecting groups removable by hydrogenolysis, these groups can be formed any conventional methods of forming an ether. These protecting groups can be removed by conventional hydrogenolysis procedures. The hyrogenolysis, according to a preferred embodiment is carried out by catalytic hydrogenation. Any conventional means of catalytic hydrogenation can be utilized in carrying out this hydrogenation step. Among the preferred methods of hydrogenation are included hydrogenating in the presence of a palladium catalyst, preferably palladium on carbon in a solvent medium consisting of an alcohol such as methanol. However, in accordance with this invention, any conventional hydrogenation catalyst such as palladium oxide, palladium chloride, etc., can be utilized. In carrying out this reaction, any conventional inert organic solvent can be utilized such as the solvent hereinbefore set forth. Among the preferred solvents for use in this reaction are included tetrahydrofuran, ethyl acetate, dioxane, diethyl ether, etc. Generally, this reaction is carried out at room temperature. However, elevated or reduced temperatures can be utilized.

The compounds of formula I are valuable antioxidants for stablizing organic materials normally susceptible to oxidation. Among these materials are included fatty materials including both solid fats and fatty oils, oxidizable hydrocarbons, including the polymeric hydrocarbons, terpenes, etc., petroleum derivatives such as waxes, mineral oils, gasoline, impregnating oils, fuel oils and the like, vitamins, essential oils such as citrus oils and the like, and similar well-known materials normally subject to oxidation.

Generally, from about 0.001% to about 0.1% by weight, based upon the weight of the material to be protected, of at least one of these antioxidants can be advantageously employed. Of course, higher and lower amounts, based on the weight of substrate, can also be used.

Fats and oils in their broad sense include animal, vegetable, fish and mineral oils, waxes, fuels, lubricants, fats greases and the like, e.g., lard, lard oil, cottonseed oil, peanut oil, lanolin, mutton tallow and grease, beef tallow, white and yellow greases, linseed oil, cod liver oil, castor oil, olive oil, coconut oil, palm oil, corn oil, paraffin oil, carnauba wax, paraffin wax, beeswax, sperm oil, keronsene, gasoline, transformer oils, essential oils, citrus oils, such as lemon oil, mono-, di- and triglycerides of various saturated and unsaturated fatty acids, hydrogenated fats and oils, etc., as well as materials containing a substantial proportion of any of the waxes, fats or oils, e.g., fish meals, certain animal feeds, paint vehicles, furniture polishes, floor waxes, automobile polishes, cottage cheese, milk, milk solids, powdered or whole eggs, egg yolks, mayonnaise, butter, margarine, salad dressing, etc. The term fats and fatty oils also includes those materials containing esters derived from glycerine, i.e., the various glycerides of the so-called fatty acids.

The following examples are illustrative but not limitative of the invention. All temperatures are in degrees centigrade and the ether used is diethyl ether.

EXAMPLE 1

A solution of 304.4 g. (2.0 mol) of trimethylhydroquinone in 1.2 liters of methanol and 300 ml. of trimethyl orthoformate was degassed, placed under $N_2$ and cooled in an ice bath to 3° centigrade. To the flask was added 5.0 ml. of concentrated aqueous sulfuric acid followed, dropwise over 3.0 hours, by 340 ml. (about 4.0 mol) of methyl vinyl ketone. The suspension was stirred without cooling for 44 hours. The mixture was worked up by extracting with diethyl ether, and washing with water, and saturated aqueous sodium bicarbonate and dried over sodium sulfate. The solvent was removed on a rotary evaporator at 30° to 50° centigrade to give ($\pm$)-6-hydroxy-2-methoxy-2,5,7,8-tetramethylchroman as a light tan solid.

EXAMPLE 2

To a solution of the ketal, ($\pm$)-6-hydroxy-2-methoxy-2,5,7,8-tetramethylchroman in 600 ml. of pyridine was added 900 ml. of acetic anhydride. The orange solution was degassed, placed under $N_2$ and stirred at 23° centigrade for 18 hours. It was then poured into 8000 ml. of ice-$H_2O$ to give a suspension which was rapidly stirred at 23° centigrade for 3.0 hours. After about 1.0 hour seeding with (±)-6-acetoxy-2-methoxy-2,5,7,8-tetramethylchroman caused the suspended oil to crystallize. The solid was removed by filtration, washed with $H_2O$, extracted with methylene chloride, washed with water, 2N aqueous hydrochloric acid and saturated aqueous sodium bicarbonate, dried over sodium sulfate and stripped of solvent to give 570 g. of red-brown oil which slowly crystallized upon standing. A similarly prepared sample was evaporatively distilled at 175°–180° centigrade/0.015 mmHg. to give analytically pure (±)-6-acetoxy-2-methoxy-2,5,7,8-tetramethylchroman as a colorless oil which soon crystallized: m.p. 71°–72.5° centigrade.

EXAMPLE 3

To a solution of (±)-6-acetoxy-2-methoxy-2,5,7,8-tetramethylchroman in 2500 ml. of acetone was added 2000 ml. of $H_2O$ followed by 16.6 ml. of concentrated aqueous HCl. Solvent was distilled from the stirred mixture until the head temperature reached 90° centigrade. The suspension was cooled in an $H_2O$ bath to 50° centigrade. At 70° centigrade, 2000 ml. of acetone was added, giving a clear solution. The solution was seeded occasionally until crystallization began. After 3.5 hours, 1500 ml. of $H_2O$ was added and the suspension was cooled in an ice bath. The solid was removed by filtration, washed with $H_2O$ and dried at 50° centigrade/0.1 mmHg. to give (±)-6-acetoxy-2-hydroxy-2,5,7,8-tetramethylchroman as a granular yellow-tan solid, sintering from 114° centigrade, m.p. 127°–132° centigrade.

EXAMPLE 4

(±)-2-ethoxy-6-hydroxy-2,5,7,8-tetramethylchroman

By the procedure of Example 1, trimethylhydroquinone and methyl vinyl ketone were condensed in ethanol and triethylorthoformate to give (±)-2-ethoxy-6-hydroxy-2,5,7,8-tetramethylchroman. The material was obtained in analytically pure form as a white powder upon crystallization from ethanol-$H_2O$; m.p. 126.5°–129.5° centigrade.

EXAMPLE 5

Alternate Preparations of (±)-6-Hydroxy-2-methoxy-2,5,7,8-tetramethylchroman

In the manner described in Example 1, 3.80 g (25 mmol) samples of trimethylhydroquinone were treated in 25 ml of methanol, 5.0 ml of trimethyl orthoformate, and 0.10 ml of 36 N aqueous $H_2SO_4$ with 50 mmole portions of the following methyl vinyl ketone substitutes: a, 2-methoxybutadiene; b, 3-ketobutanol; c, 3,3-dimethoxybutene (contaminated with about 20 percent 2-methoxybutadiene); and d, 4-methoxy-2-butanone. The reactions were monitored by tlc. Reactions a,c and d were complete after 24 hr and were worked up and dried in the manner of Example 1 to give (±)-6-hydroxy-2-methoxy-2,5,7,8-tetramethychroman. In reaction b, a>50 percent conversion to (±)-6-hydroxy-2-methoxy-2,5,7,8-tetramethylchroman was indicated by tlc.

EXAMPLE 6

(±)-(6-Hydroxy-2,5,7,8-tetramethylchroman-2-yl) acetic acid

In a dried flask under $N_2$, a suspension of 47.2 g (1.10 mol) of 56 percent by weight sodium hydride in mineral oil in 1000 ml of tetrahydrofuran was stirred as 209.4 g (1.15 mol) of trimethyl phosphonoacetate was added over 2.25 hr. The white paste was stirred for 0.25 hr and then a solution of 132.2 g (0.50 mol) of (±)-6-acetoxy-2hydroxy-2,5,7,8-tetramethylchroman in 1000 ml of tetrahydrofuran was added over 0.50 hr. The pale yellow suspension was stirred at 23° C for 18 hours and then heated at reflux for 4.0 hours. The cooled solutions from two such reactions were stripped of solvent and worked up and dried by the procedure given in Example 1 to give a cloudy red-brown oil containing (±)-methyl-(6-acetoxy-2,5,7,8-tetramethylchroman-2-yl) acetate. To a solution of this material in 2000 ml. of ethanol, there was added 2000 ml. of $H_2O$ and 240 g. (6.0 mol.) of NaOH. The solution was stirred at 23° C. for 4 hours, washed with petroleum ether (b.p. 30°–60° C.). diluted with 6000 ml. of ice-$H_2O$ and acidified by the dropwise addition over 0.50 hour of 600 ml. of concentrated aqueous HCl. The solid was removed by filtration, washed with $H_2O$ and crystallized from ethanol-$H_2O$ to give (±)-6-hydroxy-2,5,7,8-tetramethylchroman-2-yl) acetic acid as a light tan powder: m.p. 168°–171° C.

EXAMPLE 7

(±)-methyl-(6-acetoxy-2,5,7,8-tetramethylchroman-2-yl) acetate

By the procedure of Example 6, 26.43 g. (0.10 mol.) of (±)-6-acetoxy-2-hydroxy-2,5,7,8-tetramethylchroman was reacted with trimethyl phosphonoacetate and then with 80 ml. of pyridine and 120 ml. of acetic anhydride by stirring under $N_2$ overnight. The solution was poured into ice-$H_2O$ and worked up and dried in the manner of Example 2. The crude product was filtered through 750 g. of 0.05-0.2 mm silica gel with 95.5 parts by volume benzene ether and then distilled to give (±)-methyl-(6-acetoxy-2,5,7,8-tetramethylchroman-2-yl)acetate as a colorless resin: b.p. 147°–149° C./10 mmHg.

EXAMPLE 8

(±)-(6-acetoxy-2,5,7,8-tetramethylchroman-2-yl)acetic acid

A mixture of 66.1 g. (0.25 mol.) of (±)-(6-hydroxy-2,5,7,8-tetramethylchroman-2-yl)acetic acid and 250 ml. each of pyridine and acetic anhydride was stirred at 25° C. under $N_2$ for 20 hours and stripped of solvent at 40° C. to give an orange-brown oil. To a suspension of this material in 500 ml. of $H_2O$ and 100 ml. of tetrahydrofuran was added 166 g. (2.0 mol.) of $NaHCO_3$. The suspension was stirred at 25° C. for 4.0 hours, washed with ether, acidified with 2N-aqueous HCl and extracted with ether. The ether solutions were washed with saturated brine, dried over sodium sulfate and stripped of solvent to give (±)-(6-acetoxy-2,5,7,8-tetramethylchroman-2-yl)acetic acid as an orangeish resin. Crystallization from diethyl ether petroleum ether (b.p. 30°–60° C.) gave (±)-(6-acetocy-2,5,7,8-tetramethylchroman-2-yl)acetic acid as a granular white solid.

EXAMPLE 9

(±)-(6-acetoxy-2,5,7,8-tetramethylchroman-2-yl)acetaldehyde

In a dry flask, a solution of 15.32 g. (50 mmol.) of (±)-(6-acetoxy-2,5,7,8-tetramethylchroman-2-yl)a- cetic acid in 100 ml. of benzene was heated under $N_2$ to 50° C. as 21.15 ml. (0.25 mol.) of oxalyl chloride was added over 20 minutes. The solution was stirred at 50° C. for another 20 minutes, cooled and stripped of solvent to produce (±)-(6-acetoxy-2,5,7,8-tetramethylchroman-2-yl)acetyl chloride. To a solution of this acid chloride in 200 ml. of dry toluene was added 15 g. of sodium acetate and 1.5 g. of 10% by weight palladium on 90% by weight carbon and 0.30 ml. of quinoline. This mixture was hydrogenated in a Parr apparatus. After 12 hours, the uptake of $H_2$ (about 55 mmole) had virtually ceased. The catalyst was removed by filtration and the filtrates were stripped of solvent. The residue was taken up in ether, washed with 2N aqueous HCl, saturated aqueous sodium bicarbonate solution and saturated brine, dried over sodium sulfate and stripped of solvent to give 15.4 g. of light yellow solid which was chromatographed on 1 kg. of 0.063–0.2 mm silica gel. Elution with 95:5 parts by volume benzene-ethyl acetate gave 11.0 g. of light yellow resin. The material from two such reactions was combined and crystallized from acetone-petroleum ether (b.p. 30°–60° C.) to give (±)-(6-acetoxy-2,5,7,8-tetramethylchroman-2-yl)-acetaldehyde as a white powder, sint 66.5° C., m.p. 68°–70° C.

EXAMPLE 10

(±)-2,6,10-trimethylundecan-1-ol

To a solution of 70 ml. of 70% by weight of bis(2-methoxyethoxy) sodium aluminum hydride in toluene (0.25 mol) in 500 ml. of anhydrous diethyl ether was added, dropwise over 1.0 hour, 69.2 g. (0.326 mol.) of (±)-2,6,10-trimethylundecanal. The solution was stirred 1.0 hour, poured onto ice and 10N aqueous NaOH, and worked up with ether and dried as described in Example 2. Distillation of the crude product gave (±)-2,6,10-trimethylundecan-1-ol as a colorless oil; b.p. 96°–98° C./0.20 mmHg.

EXAMPLE 11

(±)-1-2,6,10-trimethylundecane

A 21.44 g. (0.10 mol) portion of (±)-2,6,10-trimethylundecan-1-ol was stirred and heated to 140° C as HBr gas was bubbled through the liquid for 4.0 hr. The two-phase mixture was cooled, diluted with petroleum ether (B.P. 30°–60° C) and washed with $H_2O$, saturated aqueous $NaHCO_3$ solution and brine. The solution was filtered through 100 g of Woelm neutral alumina III, stripped of solvent, and distilled to give (±)-1-bromo-2,6,10-trimethylundecane as a colorless liquid: bp 97°–99° C/0.10 mmHg.

EXAMPLE 12

2RS,4′RS,8′RS-2′,3′-dehydro-α-tocopherol acetate

In a dry flask, a mixture of 6.66 g (20 mmol) of (±)-1-bromo-2,6,10-trimethylundecane and 6.56 g (25 mmole) of triphenylphosphine was heated under $N_2$ at 200° for 6.0 hr. The cooled gum i.e., triphenyl-2,6,10-trimethylundecanylphosphoniumbromide was dissolved in 100 ml of glyme (freshly distilled from $CaH_2$) and stirred as 11.0 ml of 2.3M phenyllithium solution in benzene was introduced via syringe. The dark red solution containing 2,6,10-trimethylundecylindenetriphenylphosphorane was stirred at 25° C for 45 min. A solution of 2.90 g (10 mmol) of (±)-(6-acetoxy-2,5,7,8-tetramethylchroman-2-yl)acetaldehyde in 25 ml of glyme was added over 5 min and the resulting mixture was heated at 60° C for 3.0 hr. The mixture was diluted with ether, worked up and dried by the procedure of Example 2 to give an orange oil which was acetylated by stirring 18 hours under $H_2$ with 25 ml. of pyridine and 25 ml. of acetic anhydride. The resulting mixture was worked up and dried in the manner of Example 2 to give, after chromotography on 1 kg. of 0.063–0.2 mm silica gel with benzene, 2RS,4′RS,8′RS-2′,3′-dehydro-α-tocopheryl acetate which was evaporatively distilled to give a colorless resin.

EXAMPLE 13

2RS,2RS,4′RS,8′RS-α-tocopheryl acetate

A solution of the chromatographed 2RS,4′RS,8′RS-2′,3′-dehydro-α-tocopheryl acetate in 60 ml. of ethyl acetate was hydrogenated over 400 mg. of prereduced $PtO_2$. After 7.0 hours, the uptake of $H_2$ (213 ml.) had virtually ceased. The catalyst was removed by filtration and washed with fresh ethyl acetate. Solvent removal, followed by evaporative distillation gave 2RS,4′RS,-8′RS-α-tocopheryl acetate as a slightly yellowish resin, b.p. 210°–215° C./10μ.

EXAMPLE 14

S-(6-hydroxy-2,5,7,8-tetramethylchroman-2-yl)acetic acid

To a solution of 26.43 g. (0.10 mol.) of (±)-(6-hydroxy-2,5,7,8-tetramethylchroman-2-yl)acetic acid in 500 ml. of tetrahydrofuran was added 15 ml. (about 115 mmol.) of S-α-methylbenzylamine. The resulting mixture was stirred at 25° C. under $N_2$ for 1.0 hour, filtered, and stripped of solvent to give a brownish resin. Two crystallizations of this material from methanol-ether gave S-(6-hydroxy-2,5,7,8-tetramethylchroman-2-yl)acetic acid S-α-methylbenzylamine salt as shiny, cream-white prisms, sint 162° C., m.p. 164°–166° C.

EXAMPLE 15

A suspension of S-(6-hydroxy-2,5,7,8-tetramethylchroman-2-yl)acetic acid S-α-methylbenzylamine salt in 200 ml. of diethyl ether and 200 ml. of 2N aqeuous HCl was stirred at 23° C. for 1.0 hour. The ether solutions were washed with water and saturated brine, dried over sodium sulfate and stripped of solvent to produce a cream-white solid. Crystallization of this sample from ethanol $H_2O$ gave S-(6-hydroxy-2,5,7,8-tetramethylchroman-2-yl)acetic acid as a white granular solid, m.p. 145.5°–148.5° C.

EXAMPLE 16

R-(6-Hydroxy-2,5,7,8-tetramethylchroman-2-yl)acetic acid

The mother liquors from the initial crystallization of the S-acid S-salt in Example 14 were treated with 2N aqueous HCl to give 8.80 g. of acid enriched in the R-epimer, R-(6-hydroxy-2,5,7,8-tetramethylchroman-2-yl)acetic acid. Treatment of this material with R-alpha-methylbenzylamine as in Example 14, followed by two crystallizations from methanol-ether, gave analytically pure R-(6-hydroxy-2,5,7,8-tetramethylchroman-2-yl)acetic acid R-alpha-methylbenzylamine salt as small, colorless prisms: sint 158° centigrade, m.p. 164.5°–166.5 degrees centigrade.

A sample of this R-acid R-salt was treated with 2N aqueous HCl as described in Example 15 to give R-(6- hydroxy-2,5,7,8-tetramethylchroman-2-yl)acetic acid after two crystallizations from ethanol H₂O, as small, white prisms: m.p. 124°–127.5° centigrade.

EXAMPLE 17

S-(6-Hydroxy-2,5,7,8-tetramethylchroman-2-yl)acetic acid with racemization of R-enantiomer A suspension of 13.22 g (50 mmol) of (±)-(6-hydroxy-2,5,7,8-tetramethylchroman-2-yl)acetic acid in 30 ml of methanol and 170 ml of ether was stirred at 20° C as 7.5 ml (~62.5 mmol) of S-α-methylbenzylamine was added. The resulting solution was immediately seeded with the S-acid S-salt S-(6-hydroxy-2,5,7,8-tetramethylchroman-2-yl)acetic acid S-α-methylbenzyl-amine salt. Stirring and cooling, finally to −20° C, gave 7.80 g of white powder. Crystallization of this material from 25 ml of methanol and 175 ml of ether gave 6.78 g of S-acid S-salt as a white powder, mp 162.5°–165° C. Conversion of this salt to 4.5 g of S-(6-hydroxy-2,5,7,8-tetramethylchroman-2-yl)acetic acid and crystallization was carried out as described in Example 15. The mother liquors from the preparation and crystallization of the S-acid S-salt were stripped of solvent to give 19.3 g of orange-brown resin. This material was converted, as described in Example 15 to free acid, giving 8.70 g of tan solid. This acid, enriched in the R-epimer R-(6-hydroxy-2,5,7,8-tetramethylchroman-2-yl)acetic acid, was suspended in 480 ml of 12N H₂SO₄, degassed, placed under N₂, and heated at reflux for 30 hr. The resulting red-orange suspension was worked up by the procedure in Example 15 utilizing ethylacetate as the solvent to give 8.40 g of brown solid. This material was triturated with 60 ml of hot ether, cooled to −20° C, and filtered. The resulting 7.1 g of tan powder was crystallized from 25 ml each of ethanol and H₂O to give 6.88 g of (±)-acid (±)-(6-hydroxy-2,5,7,8-tetramethylchroman-2-yl)acetic acid as a light tan powder: mp 173.5°–175° C. The effective yield of S-acid S-(6-hydroxy-2,5,7,8-tetramethylchroman-2-yl)acetic acid with racemization of R-enantiomer was thus 71 percent based on a conversion of 48 percent.

EXAMPLE 18

S-(6-Acetoxy-2,5,7,8-tetramethylchorman-2-yl)acetic acid

Acetylation of the S-acid,S-(6-hydroxy-2,5,7,8-tetramethylchroman-2-yl)acetic acid, was carried out as described in Example 8. Crystallization of the crude product from acetone-hexane gave S-(6-acetoxy-2,5,7,8-tetramethylchroman-2yl)actic acid as a white power: mp 125°–126.5°.

EXAMPLE 19

S-(6-Acetoxy-2,5,7,8-tetramethylchroman-2-yl)acetaldehyde

The S-acetoxy acid, S-(6-acetoxy-2,5,7,8-tetramethylchromam-2-yl)acetic acid, was converted, as described in Example 9, via acid chloride S-(6-acetoxy-2,5,7,8-tetramethylchroman-2-yl)acetyl chloride to the desired aldehyde. Crytallization of the crude product from acetone-hexane gave S-(6-acetoxy-2,5,7,8-tetramethylchroman-2-yl)acelaldehyde as samll, colorless rods: mp 87.5°–90° C.

EXAMPLE 20

2R,6R-2,6,10-Trimethylundecan-1-ol

Phytol was dehydrated to a mixture of $\Delta^{2,4}$- and $\Delta^{3,5}$-phytadienes by the procedure published in Mayer et al., "Helv. Chim, acta"46,650 (1963). A solution of 21.25 g. (76.5 mmol.) of this phytadiene mixture, b.p. 131–140° centigrade/0.5 mmHg., in 150 ml. of pentane was cooled in a dry ice bath to -50° centigrade. Ozone (0.80–0.88 mmol./min.) was bubbled through the solution at -50° to -70° centigrade for 3.5 hours (total $O_3=\lambda$ about 175 mmol.). Nitrogen was then bubbled through the solution for 20 minutes to remove excess ozone. The ozonide solution was transferred to a cooled (-7° centigrade dropping funnel and added, dropwise over 1.5 hours, to 107 ml. of 70% by weight bis (2-methoxyethoxy) sodium aluminum hyride in toluene which was kept cold by means of an ice-salt bath (internal temp during addition 5°–8° centigrade). The solution was allowed to come to 20° centigrade, stirred at that temperature for 1.0 hour, and poured onto ice and 80 ml. of 10N aqueous NaOH. Workup with ether and drying by the procedure of Example 2 gave a pale yellow oil. The product from four such reactions (95.4 g.) was distilled through a 20 cm Vigreux column to give a mixture of 2R,6R-2,6,10-trimethylundecan-1-ol and 3R,7R-3,7,11-trimethyldodecan-1-ol. The desired C-14 alcohol 2R,6R-2,6,10-trimethylundecan-1-ol could be separated from this mixture by distillation through a spinning band or 30-cm Goodloe column and obtained as a colorless liquid: b.p. 76°–78° centigrade/0.05 mmHg.

Further distillation of the residue remaining after the separation of the C-14 alcohol gave 3R,7R-3,7,11-trimethyldodecan-1-ol.

EXAMPLE 21

2R,6R-1-Bromo-2,6,10-trimethylundecan

Treatment of the 2R,6R-alcohol 2R,-2,6,10-trimethylundecan-1-ol with HBr at 140° C by the procedure of Example 11 gave 2R,6R-1-bromo-2,6,10-trimethylundecane as a colorless oil: bp 80°–82° C/0.05 mmHg.

EXAMPLE 22

By the procedure given in Example 12, 2R,6R-1-bromo-2, 6,10-trimethylundecane was reacted with triphenylphosphine to produce triphenyl-2R,6R-2,6,10-trimethylundecanylphosphonium bromide which was then reacted with phenylithium to produce 2R,6R,-2,6,10-trimethylundecylidenetripenylphosporane. By the procedure of Example 12, the phosphorane was reacted with S-(6-acetoxy-2,5,7,8-tetramethylchroman-2-yl)acetaldehyde to produce 2R,4′R,-8′R-2′,3′-dehydro-α-tocopheryl acetate. The dehydro-α-tocopheryl acetate was hydrogenated by the procedure of Example 13 to produce 2R,4′R,8′R- α-tocopheryl acetate.

EXAMPLE 23

2R,4′R,8′R-alpha-Tocopherol

A solution of 2.8 ml. of 70% bis(2-methoxyethoxy) sodium aluminum hyride in toluene in 25 ml. of anhydrous diethyl ether was stirred as a solution of 2.36 g. (5.0 mmol.) of 2R,4′R,8′-R-alpha-tocopheryl acetate in 10 ml. of diethyl ether was added over 15 minutes. The solution was stirred an additional 1.0 hour, poured onto ice and 6N aqueous H₂SO₄ and worked up with ether and dried by the procedure givin in Examplle 2. Evaporative distillation gave 2R,4'R,8'R-alpha-tocopherol as a yellowish resin.

EXAMPLE 24

(±)-2-Carboxy-6-hyroxy-2,5,7,8-tetramethylchroman

A solution of 26.4 g. (0.1 mol.) of (35)-6-acetoxy-2-hydroxy-2,5,7,8-tetramethylchroman in 200 ml. of dimethylsulfoxide was rapidly stirred as 32.5 g. (0.5 mol.) of granular KCN was added by sifting so that a uniformly dispersed suspension was obtained. The resulting mixture was cooled to 15 degress centigrade as 47.0 ml. of 12N aqueous H₂SO₄ was added over 1.25 hours as the internal temp. was maintained at 20 degrees centigrade. Tlc at this point showed a major, slower-running spot in addition to traces of starting material. The material was poured into diethylether and H₂O. The ether solution were washed with water and brine, dired over NaSO₄ and stripped of solvent to yield (±)-2-cyano-4-(5-acetoxy-2-hyroxy-3,4,6-trimethylphenyl) butan-2-ol as a gum.

EXAMPLE 25

The cyanohdrin prepared in Example 24 was immediately taken up in 250 ml of methanol. This solution was cooled in an ice bath, saturated with anhyrous hydrochloric acid, stored for 18 hrs at -2° C and stripped of solvent on a rotary evaporator (bath temp less than 30° C). The resulting gum was taken up in 250 ml of water, degassed, placed under nitrogen and heated for 2.0 hr at 40° C to produce an aqueous suspension. The aqueous suspension was worked up and dried in the manner of Example 2 utilizing a solvent mixture of ethyl acetate and diethyl carbomethoxy-4-(2,5-hydroxy-3,5,6-trimethylphenyl)butan-2-oll and (±)-2-carbomethyoxy-6-hydroxy-2,5,7,8-tetramethychroman. This mixture was a tan solid.

The tan solid was triturated with diethyl ether and then crystallized from diethyl ether to give (±)-2-carbomethoxy-4-(2,5-hydroxy-3,5,6-trimethylphenyl)butan-2-ol as white prisms: mp 135°–136.5° C.

From the aqueous suspension prepared above, the ester (±)-2-carbomethoxy-6-hydroxy-2,5,7,8-tetramethylchroman was isolated by filtration of the aqueous suspension prior to working up.

EXAMPLE 26

The tan solid of Example 25 was suspended in 100 ml of methanol, to which was added, over 10 min, 100 ml of 2N aqueous NaOH. The resulting solution was stirred under N₂ for 24 hr, treated with 57 ml of 2N aqueous HCl followed by 10 ml of saturated aqueous NaHCO₃ solution to give a solution of pH 7.5–8.0. The solution was extracted with diethyl ether, acidified with 2N aqueous HCl and again extracted with diethyl ether. These latter extracts were washed with brine, dried (Na₂SO₄) and stripped of solvent. The resulting 24.3 g of gum which partially crystallized was shown by tlc to be an approximately equimolar mixture of cyclized and uncyclized acids. Pure uncyclized acid, (±)-2-carboxy-4-(2,5-dihydroxy-3,4,6-trimethyl)-butan-2-ol was isolated from this mixture by filtration of the aqueuos suspension obtained upon acidification, extraction with diethyl ether and crystallization from diethyl ether, as a white solid which was very susceptible to air oxidation: mp 177°–178° C.

EXAMPLE 27

The crude mixture of acids in Example 26 and 0.57 g of p-toluenesulfonic acid monohydrate in 300 ml of benzene was heated at reflux under N₂ with azeotropic removal of H₂O for 1.25 hr. The cooled solution was washed with a total of 300 ml of one-half saturated aqueous NaHCO₃ and with brine. The aqueous solutions were treated with charcoal acidified with 2N aqueous HCl and filtered to give (±)-(6-hydroxy-2,5,7,8-tetramethylchroman-2-yl)carboxylic acid as a light tan powder, mp 189°–190° C.

EXAMPLE 28

(±)-6-Acetoxy-2-carboxy-2,5,7,8-tetramethylchroman

To a partial solution of 5.0 g. (20 mmol) of (±)-2-carboxy-6-hydroxy-2,6,7,8-tetramethylchroman in 8.0 ml. of pyridine was added, dropwise over 10 minutes, 12.0 ml. of acetic anhydride. The solution was allowed to stand for 16 hours and was then worked up and dried by the procedure of Example 2 utilizing dichloromethane as a solvent to give a white solid. Crystallization from a mixture of ether-petroleum ether (b.p. 30°–60° centigrade) gave (±)-6-acetoxy-2-carboxy-2,5,7,8-tetramethylchroman.

EXAMPLE 29

The compound (±)-(6-hydroxy-2,5,7,8-tetramethylchroman-2yl)-carboxylic acid was resolved with S-alpha-methylbenezylamine by the procedure of Example 14 to produce S-(6-hydroxy-2,5,7,8-tetramethylchroman-2-yl)-carboxylic acid S-alpha-methylbenzylamine salt, m.p. 153.5°–154.0° centigrade upon crystallization from a mixture of ethanol-diethyl ether.

The mother liquors from this crystallization were treated as in Example 16 with R-alpha-methylbenzylamine to produce R-(6-hydroxy-2,5,7,8-tetramethylchroman-2-yl) carboxylic acid R-alpha-methylbenzylamine salt, m.p. 153.5°–155° centigrade upon crystallization from a mixture of ethanol-diethyl ether.

EXAMPLE 30

Both the S-acid-S-salt and R-acid-R-salt of Example 29 were treated with 2N-aqueous hydrochloric acid as in Example 15 to give S-(6-hydroxy-2,5,7,8-tetramethylchroman-2-yl) carboxylic acid and R-(6-hydroxy-2,5,7,8-tetramethylchroman-2-yl) carboxylic acid.

EXAMPLE 31

Acetylation of the S-acid of Example 30 utilizing the procedure of Example 8 produced S-(6-acetoxy-2,5,7,8-tetramethylchroman-2-yl) carboxylic acid. Acetylation of the R-acid of Example 30 utilizing the procedure of Example 8 produced R-(6-acetoxy-2,5,7,8-tetramethylchroman-2-yl) carboxylic acid.

EXAMPLE 32

To a mixture of 1.34 g. of dimethylchloroformimium chloride and 12 ml of chlorobenzene were added 2.92 g of (±) -6-acetoxy-2,5,7,8-tetramethylchroman-2-carboxylic acid. The resulting solution was heated at 110° under N₂ for 40 min and stripped of solvent to give (±) 6-acetoxy-2,5,7,8-tetramethylchroman -2-carboxylic acid chloride as a light yellow, very viscous gum. To a mixture of 2.89 mmoles of this material in 4 ml of acetone was added 0.43 ml of triethylamine and 90 mg of 10% palladium on carbon catalyst. The mixture was hydrogenated at atmospheric pressure and room temperature. Uptake ceased after 1.0 hr. The suspension was filtered and the filtrate was stripped of solvent, taken up in ether, washed with saturated aqueous sodium bicarbonate solution, 2N aqueous HCl, and brine, dried over sodium sulfate and stripped of solvent. The residue was chromatographed on silica gel with 8:2 parts by volume benzene-ethyl acetate and then crystallized from 30°–60° petroleum ether to give (±)-6-acetoxy-2,5,7,8-tetramethylchroman -2-carboxaldehyde as a white solid, m.p. 92.5°–96°.

Utilizing the above procedure, S-(6-acetoxy-2,5,7,8 tetramethylchroman-2-yl) carboxylic acid was converted to S-(6-acetoxy-2,5,7,8-tetramethylchroman-2-yl) carboxaldehyde via S-(6-acetoxy-2,5,7,8-tetramethylchroman-2-yl) carboxylic acid chloride.

Utilizing the above procedure, R-(6-acetoxy-2,5,7,8-tetramethylchroman-2carboxylic acid was converted to R-(6-acetoxy-2,5,7,8-tetramethylchroman-2-yl)- carboxyaldehyde via R-(6-acetoxy -2,5,7,8-tetramethylchroman-2-yl) carboxylic acid chloride.

EXAMPLE 33

The compound R-(6-hydroxy-2,5,7,8-tetramethylchroman-2-yl) acetic acid was acetylated in the manner of Example 18 to produce the R-acid, R-(6-acetoxy-2,5,7,8-tetramethylchroman-2-yl) acetic acid.

EXAMPLE 34

The compound R-(6-acetoxy-2,5,7,8-tetramethylchroman-2-yl) acetic acid was treated by the procedure of Example 9 to produce R-(6-acetoxy-2,5,7,8-tetramethylchroman 2-yl)acetaldehyde via R-(6-acetoxy-2,5,7,8-tetramethylchroman-2-yl)acetyl chloride.

EXAMPLE 35

By the procedure of Example 22, triphenyl-2R,6R-2,6,10-trimethylundecanyl-phosphonium bromide was reacted with S-(6-acetoxy-2,5,7,8-tetramethylchroman-2-yl)acetaldehyde to produce 2R,4′R,8′R-2′,3′-dehydroalpha-tocopheryl acetate which was hydrogenated by the procedure of Example 13 to produce 2R,4′R,8′R-alpha-tocopheryl acetate.

EXAMPLE 36

By the procedure of Example 22, triphenyl-2R,6R-2,6,10-trimethylundecanylphosphonium bromide was reacted with (±) (6-acetoxy-2,5,7,8-tetramethylchroman-2-yl) acetaldehyde to produce 2RS,4′R,8′R-2′,3′-dehydroalpha-tocopheryl acetate which was hydrogenated by the procedure of Example 13 to produce 2RS,4′R,8′R-alpha-tocopheryl acetate.

EXAMPLE 37

By the procedure of Example 22, triphenyl-2RS,6RS-2,6,10-trimethylundecanylphosphonium bromide was reacted with R-(6-acetoxy-2,5,7,8-tetramethylchroman-2yl)acetaldehyde to produce 2R,4′RS,8′RS-2′,3′-dehydroalpha-tocopheryl acetate which was hydrogenated by the procedure of Example 13 to produce 2R,4RS,8′RS-alpha-tocopheryl acetate.

EXAMPLE 38

The compounds (±)-(6-hydroxy-2,5,7,8-tetramethylchroman-2-yl) acetic acid (compound A), (±)-2-carboxy-6-hydroxy-2,5,7,8-tetramethylchroman (compound B), (±)-(6-hydroxy-2,7,8-trimethylchroman-2-yl) acetic acid (compound C), (±)-2-ethyl-6-hydroxy-5,7,8-trimethylchroman-2-carboxylic acid (compound D), (±) -6-hydroxy-5,7,8-trimethylchroman-2-carboxylic acid (compound E), (±)-6-hydroxy-2,7,8-trimethylchroman-2-carboxylic acid (compound F), (±)-7-tert-butyl-6-hydroxy-2-methylchroman-2-carboxylic acid (compound G), and (±)-6-hydroxy-5,7-diisopropyl-2-methylchroman -2-carboxylic acid (compound H) were mixed in chicken fat, pork fat and soybean oil. Each of the compounds A-H was incorporated into the fat or oil in an amount of 0.02% by weight based upon the weight of the oil or fat with which it was mixed. The oil or fat compositions were subjected to the Schaal Oven Test at 45° centigrade as described by Lindlong in Auto-Oxidation and Anti-Oxidants, Volume II (Interscience Publishers, Div. of John Wiley, New York, 1962) pages 450–453. The days necessary to reach rancidity are given in the following table:

| Compound | Chicken Fat | Pork Fat | Soybean Oil |
|---|---|---|---|
| A | 16 | 21 | 12 |
| B | 29 | Over 25 | Over 15 |
| C | 17 | — | 6 |
| D | 6 | — | 7 |
| E | 12 | — | 9 |
| F | 25 | — | 12 |
| G | 20 | — | 5 |
| H | 25 | — | 15 |
| None | 3 | 5 | 2 |

EXAMPLE 39

Trimethylhydroquninone was reacted with ethyl vinyl ketone by the procedure of Example 1 to give (±)-2-ethyl-6-hydroxy-2-methoxy-5,7,8-trimethylchroman as a beige powder, m.p. 96.5°–98.5° from methanol-$H_2O$.

EXAMPLE 40

Trimethylhydropquinone was reacted with acrylophenone by the procedure of Example 1 to give (±)-6-hydroxy-2-methoxy-2-phenyl-5,7,8-trimethylchroman as a white solid, m.p. 190.5°–192.5° from acetone-30°–60° petroleum ether.

EXAMPLE 41

Trimethylhydroquinone was reacted with acrolein by the procedure of Example 1 to give (±)-6-hydroxy-2-methoxy-5,7,8-trimethylchroman as a tan powder, m.p. 108°–110.5°, from methanol-$H_2O$.

EXAMPLE 42

Reaction of tert-butyl-hydroquninone with methyl vinyl ketone by the procedure of Example 1 gave (±)-7-tert-butyl-6-hydroxy-2-methoxy-2-methylchroman as a white solid, m.p. 115°–117° from ether-30°–60° petroleum ether.

EXAMPLE 43

Reaction of 2,6-diisopropylhydroquinone with methyl vinyl ketone by the procedure of Example 1 gave (±)-6-hydroxy-5,7,-diisopropyl-2-methoxy-2-methylchroman as a colorless resin.

EXAMPLE 44

Reaction of p-(benzyloxy)phenol with methyl vinyl ketone by the procedure of Example 1 gave (±)-6-benzyloxy-2-methoxy-2-methylchroman as a viscous, light yellow resin.

EXAMPLE 45

A mixture of 40 g. of p-(benzyloxy)phenol, 33.6 g. of 2-methoxybutadiene, and 30 ml. of benzene was sealed in a glass tube under $N_2$. The tube was heated at 160°–165° for 20 hours, cooled and opened. The yellow solution was chromatographed on silica gel with 97.5:2.5 benzene-ethyl acetate to give (±)-6-benzyloxy-2-methoxy-2-methylchroman, identical with the material prepared as described in Example 44, as 34.5 g. of pale yellow oil.

EXAMPLE 46

To a solution of the (±)-6-benzyloxy-2-methoxy-2-methylchroman prepared in Example 45 in 250 ml. of ethanol was added 2.5 g. of 10% palladium on carbon catalyst, and the resulting mixture was hydrogenated at atmospheric pressure and room temperature. After nine hours, the uptake of hydrogen (3100 ml.) had ceased. The catalyst was removed by filtration and the filtrates were stripped of solvent at reduced pressure. Crystallization of the solid residue from ether-30°–60° petroleum ether gave (±)-6-hydroxy-2-methoxy-2-methylchroman as white needles, m.p. 128°–130°.

EXAMPLE 47

By the manner of Example 45, 4-benzoyloxy-2,3-dimethylphenol was reacted with 2-methoxybutadiene to give (±)-6-benzoyloxy-2-methoxy-2,7,8-trimethylchroman as a white powder, m.p. 101.5°–102.5°, from ether-30°–60° petroleum ether.

EXAMPLE 48

Acetylation of (±)-6-hydroxy-2-methoxy-5,7,8-trimethylchroman by the method described in Example 2 gave (±)-6-acetoxy-2-methoxy-5,7,8-trimethylchroman as colorless oil.

EXAMPLE 49

By the procedure described in Example 3, (±)-6-benzoyloxy-2-methoxy-2,7,8-trimethylchroman was converted to (±)-6-benzoyloxy-2-hydroxy-2,7,8-trimethylchroman, a white solid of m.p. 101°–103.5° from ether-30°–60° petroleum ether.

EXAMPLE 50

A solution of (±)-6-acetoxy-2-methoxy-5,7,8-trimethylchroman, prepared as described in Example 2 from 0.1 mole of (±)-6-hydroxy-2-methoxy-5,7,8-trimethylchroman, in 200 ml. of 1:1 acetic acid-$H_2O$ was heated at reflux under a nitrogen atmosphere for 1.5 hours. The mixture was cooled, diluted with 200 ml. of $H_2O$ and filtered. The solid was washed with $H_2O$ and dried to give (±)-6-acetoxy-2-hydroxy-5,7,8-trimethylchroman as a white solid, m.p. 115°–120°.

EXAMPLE 51

By the procedure of Example 24, (±)-6-acetoxy-2-hydroxy-5,7,8-trimethylchroman was converted to (±)-1-cyano-3-(5-acetoxy-2-hydroxy-3,4,6-trimethylphenyl)propanol, which was obtained as a light yellow oil.

EXAMPLE 52

A solution of (±)-6-hydroxy-2,5,7,8-tetramethylchroman, prepared as described in Example 1 from 1.0 mole of trimethylhydroquinone, in 1250 ml. of acetone, 1000 ml. of $H_2O$ and 8.30 ml. of conc. HCl was heated at reflux under $N_2$. The solvent was removed by distillation until the distilling head temperature reached 95°. The suspension was cooled to 70°, diluted with 800 ml. of acetone, cooled to ca. 15° and stripped of solvent at reduced pressure and 30° to ca. 1000 ml. The resulting suspension was cooled, filtered and dried to give (±)-2,6-dihydroxy-2,5,7,8-tetramethylchroman as a grey-tan powder, m.p. 105°–107°.

EXAMPLE 53

By the method described in Example 52, (±)-2-ethyl-6-hydroxy-2-methoxy-5,7,8-trimethylchroman was converted to (±)-2,6-dihydroxy-2-ethyl-5,7,8-trimethylchroman, obtained as a light brown solid.

EXAMPLE 54

By the method described in Example 52, (±)-6-hydroxy-2-methoxy-2-phenyl-5,7,8-trimethylchroman was converted to (±)-2,6-dihydroxy-2-phenyl-5,7,8-trimethylchroman, obtained as a light powder.

EXAMPLE 55

By the method described in Example 52, (±)-6-hydroxy-2-methoxy-2-methylchroman was converted to (±)-2,6-dihydroxy-2-methylchroman, which was obtained as a light orange oil.

EXAMPLE 56

A suspension of the (±)-2,6-dihydroxy-2,5,7,8-tetramethylchroman prepared in Example 52 in 600 ml. of pyridine was placed under $N_2$. Acetic anhydride (900 ml.) was added over 1.0 hour. The resulting orange solution was stirred at 23° overnight, poured into ice-$H_2O$, stirred 2.0 hour and extracted with benzene and ether. The organic extracts were washed with 2N HCl, brine, saturated $NaHCO_3$ solution and brine and dried over $Na_2SO_4$. Solvent removal gave 4-(2,5-diacetoxy-3,4,6-trimethylphenyl)-butan-2-one as a very hard solid, m.p. 85°–87.5°.

EXAMPLE 57

By the procedure of Example 56, (±)-2,6-dihydroxy-2-ethyl-5,7,8-trimethylchroman was converted to 5-(2,5-diacetoxy-3,4,6-trimethylphenyl)-pentan-3-one, which was obtained as a white powder, m.p. 98°–100.5°, from ether.

EXAMPLE 58

By the procedure of Example 56, (±)2,6-dihydroxy-2-phenyl-5,7,8-trimethylchroman was converted to 2-(2,5-diacetoxy-3,4,6-trimethylphenyl)-ethyl phenyl ketone, which was obtained as fine white needles, m.p. 153°–154.5°, from ethylene chloride-ether.

EXAMPLE 59

By the procedure of Example 56, (±)-2,6-dihydroxy-2-methylchroman was converted to 4-(2,5-diacetoxyphenyl)butan-2-one, which was obtained as a light yellow oil.

EXAMPLE 60

A solution of the crude 4-(2,5-diacetoxy-3,4,6-trimethylphenyl) butan-2-one prepared in Example 56 in 963 ml. of dimethylformamide was cooled under $N_2$ in an ice bath. A solution of 69.4 g. of potassium cyanide in 150 ml. of $H_2O$ was added over 20 minutes. The mixture was stirred another 10 minutes and then 161 ml. of 6N $H_2SO_4$ was added dropwise over 20 minutes while an internal temperature of +10° to +13° was maintained. The viscous suspension (pH 8) was stirred another 30 minutes, brought to pH 4 by the addition of 16.5 ml. of 6N $H_2SO_4$, poured into ice-$H_2O$, and extracted with ether. The ether solutions were washed with brine, dried over $Na_2SO_4$, and stripped of solvent to give (±)-2-cyano-4-(2,5-diacetoxy-3,4,6-trimethylphenyl)butan-2-ol as an orange-brown foam.

EXAMPLE 61

By the method of Example 60, 5- (2,5-diacetoxy-3,4,6-trimethylphenyl)pentan-3-one was converted to (±)-3-cyano-5-(2,5-diacetoxy-3,4,6-trimethylphenyl)-pentan-3-ol, which was obtained as an orange oil.

EXAMPLE 62

By the method of Example 60, 4-(2,5-diacetoxyphenyl)butan-2-one was converted to (±)-2-cyano-4-(2,5-diacetoxyphenyl)butan-2-ol, which was obtained as a yellow oil.

EXAMPLE 63

A solution of the crude (±)-2-cyano-4-(2,5-diacetoxy-3,4,6-trimethylphenyl)butan-2-ol prepared in Example 60 in 2000 ml. of anhydrous methanol was cooled in a dry ice-ethanol bath. When the internal temperature reached −50°, HCl gas was passed rapidly into the solution. Over the next 45 minutes, the external and internal temperatures were allowed to come to −20° and +5°, respectively. These temperatures were maintained until the solution was saturated with HCl. The clear, dark brown solution was kept at +2° overnight, stripped of solvent at reduced pressure, diluted with 2000 ml. of $H_2O$, heated at 40° under $N_2$ for 2.0 hours, cooled and extracted with ethyl acetate and ether. The organic solutions were washed with saturated brine, dried over $Na_2SO_4$ and stripped of solvent to give (±)-methyl 4-(2,5-dihydroxy-3,4,6-trimethylphenyl)-2-hydroxy-2-methylbutanoate as a dark green-black oil. TLC indicated that under these conditions, vitrually no (±)-methyl 6-hydroxy-2,5,7,8-tetramethylchroman-2-carboxylate had been formed.

EXAMPLE 64

By the procedure of Example 25, (±)-1-cyano-3-(5-acetoxy-2-hydroxy-3,4,6-trimethylphenyl)propanol was converted to a mixture of (±)-methyl 6-hydroxy-5,7,8-trimethylchroman-2-carboxylate containing minor amounts of (±)-methyl 4-(2,5-dihydroxy-3,4,6-trimethylphenyl)-2-hydroxybutanoate as a cream-white solid.

EXAMPLE 65

By the procedure of Example 63, (±)-3-cyano-5-(2,5-diacetoxy-3,4,6-trimethylphenyl)pentan-3-ol was converted to (±)-methyl 4-(2,5-dihydroxy-3,4,6-trimethylphenyl)-2-ethyl-2-hydroxybutanoate which was obtained as an orange oil.

EXAMPLE 66

By the method described in Example 26, the crude (±)-methyl 4-(2,5-dihydroxy-3,4,6-trimethylphenyl)-2-hydroxy-2-methylbutanoate obtained in Example 63 was saponified to (±)-4-(2,5-dihydroxy-3,4,6-trimethylphenyl)-2-hydroxy-2-methylbutanoic acid, which was obtained as a tan, powdery solid.

EXAMPLE 67

The crude mixture of (±)-methyl 6-hydroxy-5,7,8-trimethylchroman-2-carboxylate and (±)-methyl 4-(2,5-dihydroxy-3,4,6-trimethylphenyl)-2-hydroxybutanoate obtained in Example 64 was converted, by the method of Example 26, to (±)-6-hydroxy-5,7,8-trimethylchroman-2-carboxylic acid and (±)-4-(2,5-dihydroxy-3,4,6-trimethylphenyl)-2-hydroxybutanoic acid. The curde mixture of acids was stirred for 0.5 hour with 250 ml. of saturated $NaHCO_3$ solution. The solution was washed with ether, treated with Darco G-60 and Norite SG-SV charcoal, filtered, acidified with 6N HCl, cooled and filtered. The solid was washed with $H_2O$, dried and crystallized from acetone-ether to give (±)-6-hydroxy-5,7,8-trimethylchroman-2-carboxylic acid as white powder, m.p. 208.5°–210° with decomposition.

EXAMPLE 68

By the method described in Example 26, (±)-methyl 4-(2,5-dihydroxy-3,4,6-trimethylphenyl)-2-ethyl-2-hydroxybutanoate was converted to (±)-4-(2,5-dihydroxy-3,4,6-trimethylphenyl)-2-ethyl-2-hydroxybutanoic acid, which was obtained in a red-orange form.

EXAMPLE 69

By the method of Example 27, the crude (±)-4-(2,5-dihydroxy-3,4,6-trimethylphenyl)-2-hydroxy-2-methylbutanoic acid obtained in Example 66 was cyclized to give (±)-6-hydroxy-2,5,7,8-tetramethylchroman-2-carboxylic acid, which was obtained in 63% overall yield from trimethylhydroquinone as a light tan powder, m.p. 188°–190°.

EXAMPLE 70

By the method of Example 27, (±)-4-(2,5-dihydroxy-3,4,6-trimethylphenyl)-2-hydroxy-2-ethylbutanoic acid was converted to (±)-2-ethyl-6-hydroxy-5,7,8-trimethylchroman-2-carboxylic acid, which was obtained as small white prisms, m.p. 21.5°–213° with decomposition, from acetone-ether.

EXAMPLE 71

(±)-2-Cyano-4-(2,5-diacetoxy-3,4,6-trimethylphenyl)butan-2-ol, prepared as described in Example 60 from 0.1 mole of 4-(2,5-diacetoxy-3,4,6-trimethylphenyl)butan-2-one, was dissolved under $N_2$ in 250 ml. of concentrated HCl. The mixture was kept at 25° for 1.5 hours and then at 60° for 44 hours. The suspension was cooled and filtered. The solid was washed with water, air dried and stirred for 1.0 hour with 360 ml. of one-half saturated $NaHCO_3$ solution and 50 ml. of ether. The aqueous phase was washed with additional ether, acidified with 6N HCl, cooled and filtered. The solid was washed with $H_2O$ and dried to give 20.64 g. (83%) of (±)-6-hydroxy-2,5,7,8-tetramethylchroman-2-carboxylic acid as a white powder, m.p. 190°–192° with decomposition.

EXAMPLE 72

Treatment of (±)-2-cyano-4-(2,5-dihydroxyphenyl)-butan-2ol with concentrated HCl as described in Example 71 gave (±)-6-hydroxy-2-methylchroman-2-carboxylic acid as a white solid, m.p. 189.5°–192°.

EXAMPLE 73

Trimethylhydroquinone (7.61 g.) was suspended under $N_2$ in 60 ml. of benzene and 15 ml. of 25% dimethylamine in $H_2O$. Aqueous formaldehyde solution (37%, 7.5 ml.) was added over 15 minutes and stirring was continued at 25° overnight. The benzene layer was washed with $H_2O$, dried over $Na_2SO_4$, and stripped of solvent to give 2-dimethylaminomethyl-3,5,6-trimethylhydroquinone as a light tan solid. A similarly prepared sample of this material, which is quite susceptible to air oxidation, had a m.p. of 103°–108.5° with decomposition, after isolation from methanol-$H_2O$.

EXAMPLE 74

To a suspension of one-half of the crude Mannich base prepared in Example 73 in 25 ml. of benzene was added 0.50 g. of hydroquinone and 15 ml. of methyl methacrylate. The materials were sealed in a glass tube under $N_2$ heated at 190° for 2.0 hours and cooled. The dark solutions were washed with 2N HCl and $H_2O$, dried over $Na_2SO_4$ and stripped of solvent. The dark residue was chromatographed on 200 g. of silica gel with 95:5 benzene-ethyl acetate and then triturated with hot ether to give (±)-methyl 6-hydroxy-2,5,7,8-tetramethylchroman-2-carboxylate as a tan solid, m.p. 158.5°–160°.

EXAMPLE 75

2-Dimethylaminomethyl-3,5,6-trimethylhydroquinone was prepared as described in Example 73 from 0.1 mole of trimethylhydroquinone. To a solution of this material in 120 ml. of benzene was added 60 ml. of methacrylonitrile and 2.0 g. of hydroquinone. The solution was sealed in a glass tube under $N_2$, heated at 190° for 1.0 hour, cooled, washed with 2N HCl and $H_2O$, dried over $Na_2SO_4$ and stripped of solvent. The dark residue was chromatographed on 500 g. of silica gel with 39:1 benzene-ethyl acetate and crystallized from ether-30°–60° petroluem ether to give (±)-2-cyano-6-hydroxy-2,5,6,8-tetramethylchroman as a tan powder, m.p. 151°–152°.

EXAMPLE 76

A suspension of 2.31 g. of (±)-2-cyano-6-hydroxy-2,5,6,8-tetramethylchroman in 50 ml. of 6N HCl was heated at reflux under $N_2$ for 16 hours, cooled and filtered. The solid was washed with $H_2O$, dried and crystallized from ether to give (±)-6-hydroxy-2,5,7,8-tetramethylchroman-2-carboxylic acid as light tan prisms, m.p. 190°–192° with decomposition.

EXAMPLE 77

By the method described in Example 6, (±)-6-benzoyloxy-2-hydroxy-2,7,8-trimethylchroman was converted to (±)-6-hydroxy-2,7,8-trimethylchroman-2-acetic acid, which was obtained as a white powder, m.p. 131°–132.5° after crystallization from benzene.

EXAMPLE 78

In a dry flask under $N_2$, a solution of 9.14 ml. (7.06 g.) of isopropylcyclohexylamine in 25 ml. of anhydrous tetrahydrofuran was cooled in an ice bath. Butyl lithium in hexane solution (2.0N, 25 ml.) was introduced via syringe (temperature to 28°). The light yellow solution was stirred another 5 minutes and then cooled to −70° in a dry ice-ethanol bath. Ethyl acetate (4.40 g.) was added over 3 minutes to the suspension (temperature to −50°). The light yellow solution of Li $^{+-}$ $CH_2COOCH_3CH_3$ was stirred 10 minutes and cooled to −70°. A solution of 3.12 g. of (±)-6-benzyloxy-2-hydroxy-2,5,7,8-tetramethylchroman in 10 ml. of tetrahydrofuran was added over 5 minutes. The resulting solution was stirred at −70° another 10 minutes, poured into 100 ml. of $H_2O$ and 7 ml. of acetic acid and extracted with ether. The ether solutions were washed with $H_2O$, saturated $NaHCO_3$ solution and brine, dried over $Na_2SO_4$ and stripped of solvent. The residue was chromatographed on 125 g. of silica gel with 9:1 and 8:2 benzene-ethyl acetate, and then crystallized from ether-30°–60° petroleum ether to give (±)-ethyl 5-(3-benzyloxy-6-hydroxy-2,4,5-trimethylphenyl)-2-hydroxy-2-methyl pentanoate as a granular white solid, m.p. 69.5°–71.5°.

EXAMPLE 79

A solution of 400 mg. of the β-hydroxyester prepared in Example 73 and 0.1 ml. of 85% phosphoric acid in 25 ml. of toluene was heated at reflux under $N_2$, with azeotropic removal of $H_2O$, for 1.0 hour. The solution was cooled, washed with $H_2O$, saturated $NaHCO_3$ solution and brine, dried over $Na_2SO_4$ and stripped of solvent. The residue was chromatographed on 25 g. of silica gel with 9:1 benzene-ethyl acetate and evaporatively distilled to give (±)-ethyl 6-hydroxy-2,5,7,8-tetramethylchroman-2-acetate as a clear resin, b.p. 150°/0.004 mm.

EXAMPLE 80

By the procedure described in Example 6, (±)-ethyl 6-hydroxy-2,5,7,8-tetramethylchroman-2-acetate was saponified to give (±)-6-hydroxy-2,5,7,8-tetramethylchroman-2-acetic acid, which was obtained as a cream-white powder, m.p. 172°–175.5°, after crystallization from ethanol-$H_2O$.

EXAMPLE 81

By the procedure described in Example 24, (±)-6-benzoyloxy-2-hydroxy-2,7,8-trimethylchroman was converted to (±)-2-cyano-4-(5-benzoyloxy-3,4-dimethyl-2-hydroxyphenyl)butan-2-ol, which was obtained as a resin.

EXAMPLE 82

By the procedure of Example 25, (±)-2-cyano-4-(5-benzoyloxy-3,4-dimethyl-2-hydroxyphenyl)butan-2-ol was converted to a mixture of (±)-methyl 6-hydroxy-2,7,8-trimethylchroman-2-carboxylic acid and (±)-methyl 4-(3,4-dimethyl-2,5-dihydroxy)-2-hydroxy-2-methylbutanoate, which was obtained as a gummy resin.

EXAMPLE 83

The mixture of methyl esters obtained in Example 82 was converted by the process described in Example 26, to a mixture of (±)-6-hydroxy-2,7,8-trimethylchroman-2-carboxylic acid and (±)-4-(3,4-dimethyl-2,5,-dihydroxy)-2-hydroxy-2-methylbutanoic acid, which was obtained as a dark semisolid.

EXAMPLE 84

The mixture of acids obtained in Example 83 was converted by the process described in Example 27 to (±)-6-hydroxy-2,7,8-trimethylchroman-2-carboxylic acid which was obtained as a powder, m.p.

167.5°–168.5° with decomposition, after crystallization from ether-30°–60° petroleum ether.

EXAMPLE 85

A mixture of 70.8 g. of (±)-6-hydroxy-2-methoxy-2,5,7,8-tetramethylchroman, 90.9 g. of anhydrous potassium carbonate, 300 ml. of dimethylsulfoxide and 69 ml. of benzyl chloride was stirred at 23° under $N_2$ for 24 hours. The suspension was poured into water and extracted with ether. The ether solutions were washed with brine, dried over sodium sulfate and stripped of solvent to give (±)-6-benzyloxy-2-methoxy-2,5,7,8-tetramethylchroman as an oil which solidified to a light yellow mass, m.p. 70°–72.5°.

EXAMPLE 86

By the procedure described in Example 3, (±)-6-benzyloxy-2-methoxy-2,5,7,8-tetramethylchroman was converted to (±)-6-benzyloxy-2-hydroxy-2,5,7,8-tetramethylchroman which was obtained as a white solid, m.p. 94.5°–95.5°, from pentane.

EXAMPLE 87

By the procedure described in Example 6, (±)-6-benzyloxy-2-hydroxy-2,5,7,8-tetramethylchroman was converted to (±)-methyl 6-benzyloxy-2,5,7,8-tetramethylchroman-2-acetate, which was obtained as a white solid, m.p. 47.5°–48.5°, after crystallization from ether-30°–60° petroleum ether.

EXAMPLE 88

By the method described in Example 6, (±)-6-benzyloxy-2-hydroxy-2,5,7,8-tetramethylchroman was converted to (±)-6-benzyloxy-2,5,7,8-tetramethylchroman-2-acetic acid, a white solid of m.p. 133.5°–134.5° after crystallization from ethanolwater.

EXAMPLE 89

By the procedure described in Example 6, (±)- 4-(2,5-diacetoxy-3,4,6-trimethylphenyl)butan-2-one was treated with the anion from trimethylphosphonoacetate. The crude (±)-methyl 5-(2,5-diacetoxy-3,4,6-trimethylphenyl)-3-methyl-2-pentenoate thus obtained, upon saponification with base as in Example 6, yielded (±)-6-hydroxy-2,5,7,8-tetramethylchroman-2-acetic acid as a light tan powder, m.p. 169°–171.5°.

EXAMPLE 90

A solution of 5.31 g. of (±)-2-cyano-4-(5-acetoxy-2-hydroxy-3,4,6-trimethylphenyl)butan-2-ol in 60 ml. of methanol was cooled in an ice bath under $N_2$. Sulfuric acid (3.8 ml.) was added over 5 minutes. The light yellow solution was stirred at 23° for 72 hours and then at reflux for 5 hours, cooled, poured into ice-$H_2O$ and filtered. The solid was washed with $H_2O$ and crystallized from ether-30°–60° petroleum ether to give (±)-2-cyano-6-hydroxy-2,5,7,8-tetramethylchroman as a white needle, m.p. 152.5°–153°.

EXAMPLE 91

To a solution of 3.54 g. of (±)-6-benzyloxy-2,5,7,8-tetramethylchroman-2-acetic acid in 35 ml. of warm ethyl acetate was added 3.24 g. of quinine followed by 25 ml. of ether. The solution was cooled to 0° and allowed to stand. The solid was removed by filtration and crystallized twice from ethyl acetate-ether to give S-6-benzyloxy-2,5,7,8-tetramethylchroman-2-acetic acid quinine salt as white needles, m.p. 163°–164°.

EXAMPLE 92

Cleavage of S-6-benzyloxy-2,5,7,8-tetramethylchroman-2-acetic acid quinine salt by the procedure described in Example 15 gave S-6-benzyloxy-2,5,7,8-tetramethylchroman-2-acetic acid as a white solid, m.p. 95.5°–96.5°, from hexane.

EXAMPLE 93

Reaction of (±)-6-benzyloxy-2,5,7,8-tetramethylchroman-2-acetic acid, by the procedure of Example 91 except with ethyl acetate alone as solvent, with R- and S-α-(1-naphthyl)ethyl amines gave S-6-benzyloxy-2,5,7,8-tetramethylchroman-2-acetic acid S-α-(1-naphthyl)ethyl amine salt, m.p. 161.5°–162.5° and R-6-benzyloxy-2,5,7,8-tetramethylchroman-2-acetic acid R-α-(1-naphthyl)ethyl amine salt, m.p. 161.5°–162°.

EXAMPLE 94

The α-(1-naphthyl)ethyl amine salts obtained in Example 93 were hydrolyzed by the procedure described in Example 15 to S-6-benzyloxy-2,5,7,8-tetramethylchroman-2-acetic acid, m.p. 95°–96° and R-6-benzyloxy-2,5,7,8-tetramethylchroman-2-acetic aicd, m.p. 94°–95°.

EXAMPLE 95

To a mixture of 0.5 g. of (±)-6-hydroxy-2,5,7,8-tetramethylchroman-2-carboxylic acid and 1.3 g. of anhydrous potassium carbonate in 3 ml. of dimethylsulfoxide was added 1.0 g. of benzyl chloride. This mixture was stirred at 23° overnight to give a solution containing (±)-benzyl 6-benzyloxy-2,5,7,8-tetramethylchroman-2-carboxylate. To this solution was added 3 ml. of 1N sodium hydroxide solution and 2 ml. of dimethylsulfoxide and the resulting 2-phase solution was stirred at 100° for 16 hours. The mixture was cooled, diluted with $H_2O$, washed with ether, acidified with 2N HCl, and extracted with ether. The ether solutions were washed with brine, dried over sodium sulfate and stripped of solvent. The residue was crystallized from ether-30°–60° petroleum ether to give (±)-6-benzyloxy-2,5,7,8-tetramethylchroman-2-carboxylic acid as a white solid, m.p. 154.5°–155°.

EXAMPLE 96

To a mixture of 32.0 g. of S-6-hydroxy-2,5,7,8-tetramethylchroman-2-acetic acid and 50.5 g. of anhydrous sodium bicarbonate in 125 ml. of dimethylsulfoxide was added 37.5 ml. of methyl iodide. The mixture was stirred at 20° under $N_2$ for 6.0 hours, poured into $H_2O$, and extracted with ether. The ether solutions were washed with $H_2O$ and brine, dried with sodium sulfate and stripped of solvent to give crude S-methyl 6-hydroxy-2,5,7,8-tetramethylchroman-2-acetate as an orangish resin. This material was acetylated in the manner described in Example 2 with 100 ml. of acetic anhydride and 150 ml. of pyridine to give S-methyl 6-acetoxy-2,5,7,8-tetramethylchroman-2-acetate as a flocculent white powder, m.p. 75.5°–78°, after crystallization from 30°–60° petroleum ether.

EXAMPLE 97

A mixture of 25.0 g. of (±)-6-hydroxy-2,5,7,8-tetramethylchroman-2-carboxylic acid, 100 ml. of 1,2-dichloroethane, 17.5 ml. of ethanol and 1.0 ml. of concentrated $H_2SO_4$ was heated at reflux under $N_2$ for 20 hours. The dark mixture was washed with $H_2O$, saturated sodium bicarbonate solution and brine, dried over sodium sulfate and stripped of solvent to give a light yellow solid. Crystallization from ether gave (±)-ethyl 6-hydroxy-2,5,7,8-tetramethylchroman-2-carboxylate, m.p. 124°–126°.

EXAMPLE 98

By the method of Example 97, (±)-6-hydroxy-2,5,7,8-tetramethylchroman-2-carboxylic acid was converted to (±)-methyl 6-hydroxy-2,5,7,8-tetramethylchroman-2-carboxylate, obtained as white prisms, m.p. 158.5°–161.5° from acetone.

EXAMPLE 99

By the method of Example 97, (±)-6-benzyloxy-2,5,7,8-tetramethylchroman-2-acetic acid was converted to (±)-methyl 6-benzyloxy-2,5,7,8-tetramethylchroman-2-acetate, which was obtained as a pale yellow oil, b.p. 195°–205°/0.03 mm., which solidified to a solid of m.p. 47.5°–48.5°.

EXAMPLE 100

A solution of 708 mg. of S-6-benzyloxy-2,5,7,8-tetramethylchroman-2-acetic acid in 10 ml. of ether was added over 15 minutes to an ice-cooled solution of about 4.0 mmoles of diazomethane in 45 mls. of ether. The solution was stirred at 3°–5° for 1.0 hour, quenched with a few drops of acetic acid, washed with $H_2O$ and brine, dried over sodium sulfate, and stripped of solvent. The residue was crystallized from hexane and 30°–60° petroleum ether to give S-methyl 6-benzyloxy-2,5,7,8-tetramethylchroman-2-acetate as a white solid, m.p. 51°–52°.

EXAMPLE 101

A solution of 31.17 g. of (±)-methyl 6-benzyloxy-2,5,7,8-tetramethylchroman-2acetate in 3.11. of pentane was cooled under $N_2$ to −70° Diisobutylaluminum hydride (24.4% in toluene; 87.3 ml.) in 87 ml. of pentane was added over 14 minutes. After 1.0 hour at −70°, another 8.73 ml. of diisobutylaluminum hydride was added and stirring was continued an additional 0.25 hour. The reaction was quenched by the careful addition of 250 ml. of methanol at −70°. The mixture was diluted with 1.01. of ether, washed with 0.5 N HCl, $H_2O$, and brine and dried over sodium sulfate. Solvent removal gave a light yellow oil, which was filtered through 500 g. of silica gel with 90:10 benzene-ethyl acetate. Crystallization of the resulting oil from hexane- - 30°–60° petroleum ether gave (±)6-benzyloxy-2,5,7,8-tetramethylchroman —2-acetaldehyde as a white solid, m.p. 70°–75°.

EXAMPLE 102

Reduction of S-methyl 6-benzyloxy-2,5,7,8-tetramethylchroman-2-acetate in the manner described in Example 101 gave S-6-benzyloxy-2,5,7,8-tetramethylchroman-2-acetaldehyde as a white solid, m.p. 87.5°–90° from 30°–60° petroleum ether.

EXAMPLE 103

(±)-2-cyano-6-hydroxy-2,5,7,8-tetramethylchroman was acetylated by the procedure described in Example 2 to give (±)-6-acetoxy-2-cyano-2,5,7,8-tetramethylchroman.

EXAMPLE 104

(±)-6-acetoxy-2-cyano-2,5,7,8-tetramethylchroman was reduced with diisobutylaluminum hydride as described in Example 101, with tetrahydrofuran as reaction solvent. TLC of the crude product indicated that it was partially deacetylated. The material was thus reacetylated by the process described in Example 2 to give (±)-6-acetoxy-2,5,7,8-tetramethylchroman-2-carboxaldehyde as a white solid, m.p. 88°–90°, from 30°–60° petroleum ether.

EXAMPLE 105

By the method of Example 9, (±)-6-benzyloxy-2,5,7,8-tetramethylchroman-2-acetic acid was converted, via (±)-6-benzyloxy-2,5,7,8-tetramethylchroman-2-acetyl chloride, to (±)-6-benzyloxy-2,5,7,8-tetramethylchroman-2-acetaldehyde, which was obtained as an oil which crystallized to a solid of m.p. 65°–67.5°.

EXAMPLE 106

To an ice-cooled mixture of 3.37 g. of aluminum chloride and 40 ml. of methylene chloride was added, dropwise, 3.37 ml. of nitromethane. The resulting solution was stirred 5 minutes, and then 5.114 g. of trimethylhydroquinone was added in one portion. The green mixture was cooled to −20° and a solution of 5.35 g. of 3-hydroxy-3-methyl-4-pentenyl acetate in 20 ml. of methylene chloride was added over 1.0 hour. The mixture was allowed to warm to room temperature, kept there for 2 hours and poured into ice-$H_2O$. The mixture was extracted with methylene chloride and the organic solutions were washed with saturated sodium bicarbonate solution and brine and dried over sodium sulfate. Solvent removal gave crude (±)-2-(2-acetoxyethyl)-6-hydroxy-2,5,7,8-tetramethylchroman as a red oil.

EXAMPLE 107

The crude (±)-2-(2-acetoxyethyl)-6-hydroxy-2,5,7,8-tetramethylchroman obtained in Example 106 was benzylated by the procedure described in Example 85 to give (±)-2-(2-acetoxyethyl)-6-benzyloxy-2,5,7,8tetramethylchroman, a colorless solid, m.p. 58°–62°, from ethanol.

EXAMPLE 108

To a solution of 0.5 g. of (±)-2-(2-acetoxyethyl)-6-benzyloxy-2,5,7,8-tetramethylchroman in 15 ml. of methanol was added a solution of 358 mg. of potassium carbonate in 1.5 ml. of water. The mixture was heated at reflux under $N_2$ for 40 minutes, cooled, poured into water and extracted with methylene chloride. The methylene chloride solutions were washed with brine, dried over magnesium sulfate and stripped of solvent to give (±)-6-benzyloxy-2-(2-hydroxyethyl)-2,5,7,8-tetramethylchroman as an oil.

EXAMPLE 109

To a mixture of 2.37 g. of pyridine in 30 ml. of methylene chloride was added 1.20 g. of chromium trioxide. The mixture was stirred for 15 minutes and then a solution of 680 mg. of (±)-6-benzyloxy-2-(2-hydroxyethyl)-2,5,7,8-tetramethylchroman in 5 ml. of methylene chloride was added. The mixture was stirred another 15 minutes and decanted from a black tar which was washed with several portions of ether. The combined organic solutions were washed with 1 N NaOH, 1 N HCl, $H_2O$, saturated $NaHCO_3$ solution and brine, dried over sodium sulfate, and stripped of solvent. The residual oil was chromatographed on 100 g. of silica gel with 9:1 benzene-ethyl acetate to give 608 mg. (90%) of (±)-6-benzyloxy-2,5,7,8-tetramethylchroman-2-acetaldehyde as a white solid, m.p. 65°-68°.

EXAMPLE 110

To a solution of 6.09 g. of (±)-6-benzyloxy-2,5,7,8-tetramethylchroman-2-acetaldehyde in 280 ml. of ethanol, was added a solution of 3.57 g. of silver nitrate in 42 ml. of $H_2O$ followed, dropwise over 0.5 hour, by a solution of 3.49 g. of sodium hydroxide in 100 ml. of $H_2O$. The mixture was stirred at 23° for 2.0 hours, filtered, concentrated in vacuo, diluted with $H_2O$, and extracted with ether. The aqueous solution was acidified with 1 N HCl and again extracted with ether. These latter extracts were washed with brine, dried over magnesium sulfate and striped of solvents to give (±)-6-benzyloxy-2,5,7,8-tetramethylchroman-2-acetic acid.

EXAMPLE 111

Triphenyl-2,6,10-trimethylundecanylphosphonium bromide was prepared and reacted with (±)-6-benzyloxy-2,5,7,8-tetramethylchroman-2-acetaldehyde by the procedures in Example 12 to give 2RS, 4'RS, 8'RS, 2',3'-dehydro-alpha-tocopheryl benzyl ether as a resin.

EXAMPLE 112

To a solution of 0.34 g. of 2RS, 4'RS, 8'RS-2',3'-dehydro-alphatocopheryl benzyl ether in 10 ml. of ethanol was added 100 mg. of 10% palladium on carbon catalyst. The mixture was hydrogenated at atmospheric pressure, filtered, and stripped of solvent to give 2RS, 4'RS, 8'RS-alpha-tocopherol. Acetylation of this material as in Example 12 gave 2RS, 4'RS, 8'RS-alpha-tocopheryl acetate as a very light yellow resin, b.p. 195°/0.02 mm.

EXAMPLE 113

To 486 mg. of magnesium powder in a dry flask under $N_2$ was added a few milliliters of a solution of 4.70 g. of 2RS, 6RS-2,6,10-trimethylundecanylbromide in 25 ml. of tetrahydrofuran. The mixture was heated to reflux, when reaction began. The rest of the bromide was added over 30 minutes and heating was continued an additional 30 minutes. A solution of 3.38 g. of (±)-6-benzyloxy-2,5,7,8-tetramethylchroman-2-acetaldehyde in 25 ml. of tetrahydrofuran was added over 10 minutes and heating was continued another 2 hours. The mixture was cooled, poured onto ice and 2 N HCl and extracted with ether. The ether solutions were washed with 2 N HCl, $H_2O$ and brine, dried over sodium sulfate, and stripped of solvent. The residue was chromatographed on silica gel with 97.5:2.5 benzene-ethyl acetate to give 2RS, 2'RS, 4'RS, 8'RS-2'-hydroxy-alphatocopheryl benzyl ether as a light yellow oil.

EXAMPLE 114

A solution of the 2RS, 2'RS, 4'RS, 8'RS-2'-hydroxy-alpha-tocopheryl benzyl ether prepared in Example 113 in 25 ml. of pyridine was cooled in an ice bath under $N_2$. Phosphorous oxychloride (2.0 ml. ) was added and the white suspension was stirred at 3° for 0.5 hours and then without cooling overnight. The mixture was poured onto ice and extracted with ether. The ether solutions were washed with 2N NaOH, $H_2O$, 2 N HCl and brine, dried over sodium sulfate and stripped of solvent. The residue was chromatographed on silica gel with 95:5 30-60° petroleum ether-ether to give a mixture of 2RS, 4'RS, 8'RS-2'3'-dehydro-alpha-tocopheryl benzyl ether and 2RS, 4'RS, 8'RS-1'2'-dehydro-alpha-tocopheryl benzyl ether as a yellow-orange resin.

EXAMPLE 115

The mixture of ethers obtained in Example 114 was hydrogenated and acetylated in the manner described in Example 112 to give 2RS, 4'RS, 8'RS-alpha-tocopheryl acetate as a light yellow, clear resin, b.p. 210°/0.035 mm.

EXAMPLE 116

By the method of Example 52, (±)-6-hydroxy-5,7-diisopropyl-2-methoxy-2-methylchroman was converted to (±)-2,6-dihydroxy-5,7-diisopropyl-2-methylchroman, which was obtained as a red-orange oil. Acetylation of this material by the method of Example 56 gave 4-(2,5-diacetoxy-4,6-diisopropylphenyl)butan-2-one, m.p. 108.5-112°.

EXAMPLE 117

By the method of Example 60, 4-(2,5-diacetoxy-4,6-diisopropylphenyl)butan-2-one was converted to (±)-2-cyano-4-(2,5-diacetoxy-4,6-diisopropylphenyl)butan-2-ol, which was obtained as a colorless oil. Treatment of this cyanohydrin with concentrated hydrochloric acid, as in Example 71, gave (±)-6-hydroxy-5,7-diisopropyl-2-methylchroman-2-carboxylic acid, m.p. 187.5-190°.

EXAMPLE 118

By the procedure of Example 1, methyl vinyl ketone was reacted with tert.-butylhydroquinone to give (±)-7-tert.butyl-6-hydroxy-2-methoxy-2-methylchroman. Hydrolysis of this material, as in Example 52, gave (±)-7-tert.-butyl-2,6-dihydroxy2-methylchroman. By the method of Example 56 acetylation of this compound gave 4-(2,5-diacetoxy-4-tert.-butylphenyl)butan-2-one, m.p. 66.5- -68°.

EXAMPLE 119

By the method of Example 60, 4-(2,5-diacetoxy-4-tert.-butylphenyl)butan-2-one was converted to (±)-2-cyano-4-(2,5-diacetoxy-4-tert.-butylphenyl)butan-2-ol. Treatment of this cyanohydrin with concentrated hydrochloric acid as in Example 71 gave a mixture of (±)-7-tert.-butyl-6-hydroxy-2-methylchroman-2-carboxylic acid and ±)-6-hydroxy-2-methylchroman-2-carboxylic acid. A mixture of 4.16 g. of these acids, 10 ml. of isobutylene, 15 ml. of toluene and 1.0 ml. of 85% phosphoric acid was heated in a sealed tube for 4.0 hours. The mixture was cooled, diluted with ether, washed with water and saturated $NaHCO_3$ solution and dried ($Na_2SO_4$). Solvent removal gave a red-orange oil which was chromatographed on 250 g. of silica gel with 85:13:2 benzene-ethyl acetate-acetic acid.

The resultant solid was crystallized from ether-30°-60° petroleum ether to give pure (±)-7-tert.-butyl-6-hydroxy-2-methylchroman-2-carboxylic acid, m.p. 218°-221°/dec.

EXAMPLE 120

To a solution of 11.0 g. of diisopropylamine in 50 ml. of anhydrous tetrahydrofuran at 0° was added 50 ml. of 2N butyllithium solution. To the resultant solution of lithium diisopropylamide was added a solution of 3.54 g. of (R)-6-benzyloxy-2,5,7,8-tetramethylchroman-2-acetic acid in 25 ml. of tetrahydrofuran. The resulting mixture was heated at 50° for 4 hours, acidified with 2N HCl and extracted with ether. The ether solutions were washed with brine, dried ($Na_2SO_4$) and stripped of solvent to give (±)-6-benzyloxy-2,5,7,8-tetramethyl-chroman-2-acetic acid, $[\alpha]_D^{25} = \pm 0°$, m.p. 130-133°.

EXAMPLE 121

A mixture of 3.38 g. of (±)-6-benzyloxy-2,5,7,8-tetramethylchroman-2-acetaldehyde, 5 ml. of benzylamine, 10 mg. of p-toluenesulfonic acid and 50 ml. of benzene was heated at reflux, under $N_2$, with azeotropic removal of $H_2O$, for 2.0 hours. The resultant solution was cooled and 2.25 g. of d-camphorsulfonic acid was added. After 1.0 hour, the resultant salt was removed by filtration and crystallized twice from ethanol-ether under $N_2$. The resolved salt was stirred under $N_2$ for 1.0 hour with a mixture of 50 ml. of ether, 10 ml. of acetic acid and 40 ml. of water. The ether layer was washed with $H_2O$, 2N HCl, $H_2O$, saturated $NaHCO_3$ solution and brine and dried ($Na_2SO_4$). Solvent removal gave optically pure 6-benzyloxy-2,5,7,8-tetramethylchroman-2-acetaldehyde, m.p. 85 -88°.

EXAMPLE 122

By the method of Example 109 2RS,2'RS,4'RS,8'RS-2'-hydroxy-α-tocopheryl benzyl ether was oxidized to 2RS,4'RS,8'RS2'-oxo-α-tocopheryl benzyl ether, a pale yellow oil.

EXAMPLE 123

A mixture of 1.0 g. of 2RS,4'RS,8'RS-2'-oxo-α-tocopheryl benzyl ether, 350 mg. of potassium hydroxide, 0.25 ml. of 85% hydrazine and 25 ml. of diethylene glycol was heated at reflux for 1.0 hour. The mixture was distilled until the internal temperature reached 205°. The mixture was kept at this temperature for 3 hours, cooled and extracted with ether. The ether solutions were washed with 2N HCL and brine and dried ($Na_2SO_4$). Solvent removal gave crude 2RS,4'RS,8'RS-α-tocopheryl benzyl ether. Debenzylation and acetylation of this material, as in Example 112, gave 2RS,4'RS,8'RS-α-tocopheryl acetate, b.p. 200 -205°/25 μ.

We claim:

1. A compound of the formula:

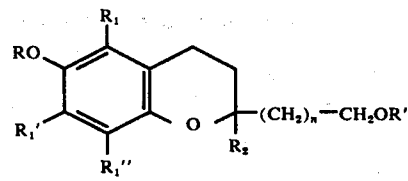

wherein $R_1$, $R_1'$ and $R_1''$ are hydrogen or lower alkyl; $R_2$ is hydrogen, lower alkyl or phenyl; R and R' are hydrogen, benzyl, benzhydryl, trityl, alpha-lower alkoxy lower alkyl, tetrahydropyranyl or an acyl moiety derived from the group consisting of a lower alkanoic acid, an aryl lower alkanoic acid, a lower alkane dicarboxylic acid, phosphoric acid and carbonic acid; and n is an integer from 0 to 1.

2. The compound of claim 1 wherein said compound is (±)-6-hydroxy-2-(2-hydroxyethyl)-2,5,7,8-tetramethylchroman.

* * * * *